US010758363B2

(12) United States Patent
Davis et al.

(10) Patent No.: US 10,758,363 B2
(45) Date of Patent: Sep. 1, 2020

(54) TRANSFORAMINAL INTERSOMATIC CAGE FOR AN INTERVERTEBRAL FUSION GRAFT AND AN INSTRUMENT FOR IMPLANTING THE CAGE

(71) Applicant: LDR Medical, Sainte-Savine (FR)

(72) Inventors: Reginald J. Davis, Cockeysville, MD (US); Kevin Kaufman, Fort Worth, TX (US); Gregory A Hoffman, Fort Wayne, IN (US); Alan W McGee, Fort Wayne, IN (US); Jean Huppert, L'etrat (FR); Hugues Mousselard, Paris (FR); Ludovic Rillardon, Le Raincy (FR)

(73) Assignee: LDR Medical, Rosieres Pres Troyes (FR)

( * ) Notice: Subject to any disclaimer, the term of this patent is extended or adjusted under 35 U.S.C. 154(b) by 177 days.

(21) Appl. No.: 15/659,602

(22) Filed: Jul. 25, 2017

(65) Prior Publication Data
US 2018/0008430 A1 Jan. 11, 2018

Related U.S. Application Data

(63) Continuation of application No. 13/585,063, filed on Aug. 14, 2012, now Pat. No. 9,713,535, which is a (Continued)

(30) Foreign Application Priority Data

Feb. 15, 2006 (FR) ..................................... 06 01315

(51) Int. Cl.
*A61F 2/44* (2006.01)
*A61F 2/46* (2006.01)
(Continued)

(52) U.S. Cl.
CPC .......... *A61F 2/4455* (2013.01); *A61F 2/4611* (2013.01); *A61F 2002/2835* (2013.01);
(Continued)

(58) Field of Classification Search
CPC .. A61F 2/44; A61F 2/46; A61F 2/4455; A61F 2/4611
See application file for complete search history.

(56) References Cited

U.S. PATENT DOCUMENTS

| 344,683 A | 6/1886 | Sherer |
|---|---|---|
| 1,025,596 A | 5/1912 | Strawser |

(Continued)

FOREIGN PATENT DOCUMENTS

| DE | 3741493 A1 | 6/1989 |
|---|---|---|
| DE | 4323034 C1 | 7/1994 |

(Continued)

OTHER PUBLICATIONS

U.S. Appl. No. 11/378,165 U.S. Pat. No. 8,409,288, filed Mar. 17, 2006, Transforaminal Intersomatic Cage for an Intervertebral Fusion Graft and an Instrument for Implanting the Cage.
(Continued)

*Primary Examiner* — Christopher J Beccia
(74) *Attorney, Agent, or Firm* — Schwegman Lundberg & Woessner, P.A.

(57) ABSTRACT

This disclosure presents various embodiments of a transforaminal intersomatic cage for an intervertebral fusion graft, and an instrument and method for implanting the cage, an embodiment of the cage having a body in the shape of a circular arc and comprising a lateral concave surface, a lateral convex surface, a straight upper surface, a straight lower surface and an end wall having at least one hole, called the end hole, designed to receive a rod of an instrument for implanting the cage between the vertebrae, wherein: the end
(Continued)

hole has an orientation that is more or less tangential to the circular arc described by the body; the extremity opposite to the end wall of the body includes a return part extending the body toward the center of the circle on which the circular arc described by the body lies.

14 Claims, 6 Drawing Sheets

Related U.S. Application Data continuation of application No. 12/279,664, filed as application No. PCT/IB2007/000367 on Feb. 15, 2007, now Pat. No. 8,241,359.

(51) Int. Cl.
   *A61F 2/28*      (2006.01)
   *A61F 2/30*      (2006.01)
(52) U.S. Cl.
   CPC ............... *A61F 2002/3008* (2013.01); *A61F 2002/30131* (2013.01); *A61F 2002/30192* (2013.01); *A61F 2002/30308* (2013.01); *A61F 2002/30576* (2013.01); *A61F 2002/30579* (2013.01); *A61F 2002/30594* (2013.01); *A61F 2002/30795* (2013.01); *A61F 2002/30845* (2013.01); *A61F 2002/30879* (2013.01); *A61F 2002/30884* (2013.01); *A61F 2002/30892* (2013.01); *A61F 2002/30894* (2013.01); *A61F 2002/4627* (2013.01); *A61F 2230/0013* (2013.01); *A61F 2230/0041* (2013.01); *A61F 2230/0063* (2013.01); *A61F 2250/0098* (2013.01)

(56) References Cited

U.S. PATENT DOCUMENTS

| | | |
|---|---|---|
| 1,121,484 A | 12/1914 | Crites |
| 3,374,786 A | 3/1968 | Callender, Jr. |
| 3,791,380 A | 2/1974 | Dawidowski |
| 3,867,728 A | 2/1975 | Stubstad et al. |
| 3,875,595 A | 4/1975 | Froning |
| 3,892,232 A | 7/1975 | Neufeld |
| 3,948,262 A | 4/1976 | Zaffaroni |
| 4,009,712 A | 3/1977 | Burstein et al. |
| 4,135,506 A | 1/1979 | Ulrich |
| 4,175,555 A | 11/1979 | Herbert |
| 4,237,875 A | 12/1980 | Termanini |
| 4,349,921 A | 9/1982 | Kuntz |
| 4,379,451 A | 4/1983 | Getscher |
| 4,409,974 A | 10/1983 | Freedland et al. |
| 4,432,358 A | 2/1984 | Fixel |
| 4,488,543 A | 12/1984 | Tornier |
| 4,494,535 A | 1/1985 | Haig |
| 4,507,115 A | 3/1985 | Kambara et al. |
| 4,519,100 A | 5/1985 | Wills et al. |
| 4,561,432 A | 12/1985 | Mazor |
| 4,599,086 A | 7/1986 | Doty |
| 4,612,920 A | 9/1986 | Lower |
| 4,621,629 A | 11/1986 | Koeneman |
| 4,632,101 A | 12/1986 | Freedland |
| 4,653,489 A | 3/1987 | Tronzo |
| 4,657,001 A | 4/1987 | Fixel |
| 4,714,469 A | 12/1987 | Kenna |
| 4,721,103 A | 1/1988 | Freedland |
| 4,759,352 A | 7/1988 | Lozier |
| 4,787,378 A | 11/1988 | Sodhi |
| 4,790,303 A | 12/1988 | Stefee |
| 4,791,918 A | 12/1988 | Von Hasselbach |
| 4,820,305 A | 4/1989 | Harms et al. |
| 4,834,757 A | 5/1989 | Brantigan |
| 4,863,476 A | 9/1989 | Shepperd |
| 4,892,545 A | 1/1990 | Day et al. |
| 4,898,156 A | 2/1990 | Gatturna et al. |
| 4,904,261 A | 2/1990 | Dove et al. |
| 4,917,704 A | 4/1990 | Frey et al. |
| 4,919,667 A | 4/1990 | Richmond |
| 4,946,468 A | 8/1990 | Li |
| 4,955,908 A | 9/1990 | Frey et al. |
| 4,964,403 A | 10/1990 | Karas et al. |
| 4,968,315 A | 11/1990 | Gatturna |
| 4,969,887 A | 11/1990 | Sodhi |
| 4,973,332 A | 11/1990 | Kummer |
| 4,973,333 A | 11/1990 | Treharne |
| 4,997,432 A | 3/1991 | Keller |
| 5,002,550 A | 3/1991 | Li |
| 5,007,910 A | 4/1991 | Anapliotis et al. |
| 5,032,125 A | 7/1991 | Durham et al. |
| 5,041,114 A | 8/1991 | Chapman et al. |
| 5,041,116 A | 8/1991 | Wilson |
| 5,046,513 A | 9/1991 | Gatturna et al. |
| 5,057,103 A | 10/1991 | Davis |
| 5,062,851 A | 11/1991 | Branemark |
| 5,071,437 A | 12/1991 | Steffee |
| 5,087,266 A | 2/1992 | Connell et al. |
| 5,098,433 A | 3/1992 | Freedland |
| 5,116,336 A | 5/1992 | Frigg |
| 5,129,901 A | 7/1992 | Decoste |
| 5,176,681 A | 1/1993 | Lawes et al. |
| 5,192,303 A | 3/1993 | Gatturna et al. |
| 5,192,327 A | 3/1993 | Brantigan |
| 5,207,679 A | 5/1993 | Li |
| 5,217,486 A | 6/1993 | Rice et al. |
| 5,242,448 A | 9/1993 | Pettine et al. |
| 5,246,458 A | 9/1993 | Graham |
| 5,300,074 A | 4/1994 | Frigg |
| 5,306,307 A | 4/1994 | Senter et al. |
| 5,306,309 A | 4/1994 | Wagner et al. |
| 5,320,644 A | 6/1994 | Baumgartner |
| 5,324,292 A | 6/1994 | Meyers |
| 5,326,205 A | 7/1994 | Anspach, Jr. et al. |
| 5,342,394 A | 8/1994 | Matsuno et al. |
| 5,344,459 A | 9/1994 | Swartz |
| 5,356,410 A | 10/1994 | Pennig |
| 5,356,413 A | 10/1994 | Martins et al. |
| 5,372,599 A | 12/1994 | Martins |
| 5,397,364 A | 3/1995 | Kozak et al. |
| 5,417,692 A | 5/1995 | Goble et al. |
| 5,417,712 A | 5/1995 | Whittaker et al. |
| 5,425,772 A | 6/1995 | Brantigan |
| 5,429,641 A | 7/1995 | Gotfried |
| 5,437,674 A | 8/1995 | Worcel |
| 5,443,514 A | 8/1995 | Steffee |
| 5,456,721 A | 10/1995 | Legrand |
| 5,458,601 A | 10/1995 | Young, Jr. et al. |
| 5,458,638 A | 10/1995 | Kuslich et al. |
| 5,472,452 A | 12/1995 | Trott |
| 5,478,342 A | 12/1995 | Kohrs |
| 5,489,210 A | 2/1996 | Hanosh |
| 5,501,695 A | 3/1996 | Anspach, Jr. et al. |
| 5,507,754 A | 4/1996 | Green et al. |
| 5,507,816 A | 4/1996 | Bullivant |
| 5,522,845 A | 6/1996 | Wenstrom, Jr. |
| 5,522,899 A | 6/1996 | Michelson |
| 5,531,792 A | 7/1996 | Huene |
| 5,534,004 A | 7/1996 | Santangelo |
| 5,534,029 A | 7/1996 | Shima |
| 5,534,030 A | 7/1996 | Navarro et al. |
| 5,545,229 A | 8/1996 | Parsons et al. |
| 5,549,617 A | 8/1996 | Green et al. |
| 5,554,191 A | 9/1996 | Lahille et al. |
| 5,562,689 A | 10/1996 | Green et al. |
| 5,571,104 A | 11/1996 | Li |
| 5,571,109 A | 11/1996 | Bertagnoli |
| 5,571,189 A | 11/1996 | Kuslich |
| 5,578,035 A | 11/1996 | Lin |
| 5,591,168 A | 1/1997 | Judet et al. |
| 5,593,409 A | 1/1997 | Michelson |
| 5,609,635 A | 3/1997 | Michelson |
| 5,609,636 A | 3/1997 | Kohrs et al. |

(56) References Cited

U.S. PATENT DOCUMENTS

| | | |
|---|---|---|
| 5,613,974 A | 3/1997 | Andreas et al. |
| 5,620,012 A | 4/1997 | Benderev et al. |
| 5,643,321 A | 7/1997 | Mcdevitt |
| 5,658,335 A | 8/1997 | Allen |
| 5,683,394 A | 11/1997 | Rinner |
| 5,683,463 A | 11/1997 | Godefroy et al. |
| 5,702,449 A | 12/1997 | Mckay |
| 5,713,899 A | 2/1998 | Marnay et al. |
| 5,741,253 A | 4/1998 | Michelson |
| 5,755,798 A | 5/1998 | Papavero et al. |
| 5,766,252 A | 6/1998 | Henry et al. |
| 5,766,253 A | 6/1998 | Brosnahan, III |
| 5,772,661 A | 6/1998 | Michelson |
| 5,776,199 A | 7/1998 | Michelson |
| 5,782,830 A | 7/1998 | Farris |
| 5,782,919 A | 7/1998 | Zdeblick et al. |
| 5,797,909 A | 8/1998 | Michelson |
| 5,800,547 A | 9/1998 | Schafer et al. |
| 5,800,550 A | 9/1998 | Sertich |
| 5,810,820 A | 9/1998 | Santori et al. |
| 5,849,004 A | 12/1998 | Bramlet |
| 5,860,973 A | 1/1999 | Michelson |
| 5,861,041 A | 1/1999 | Tienboon |
| 5,865,845 A | 2/1999 | Thalgott |
| 5,888,222 A | 3/1999 | Coates et al. |
| 5,888,223 A | 3/1999 | Bray, Jr. |
| 5,888,224 A | 3/1999 | Beckers et al. |
| 5,888,227 A | 3/1999 | Cottle |
| 5,888,228 A | 3/1999 | Knothe et al. |
| 5,895,427 A | 4/1999 | Kuslich et al. |
| 5,897,556 A | 4/1999 | Drewry et al. |
| 5,968,098 A | 10/1999 | Winslow |
| 5,976,139 A | 11/1999 | Bramlet |
| 5,980,522 A | 11/1999 | Koros et al. |
| 5,984,967 A | 11/1999 | Zdeblick et al. |
| 5,989,289 A | 11/1999 | Coates et al. |
| 6,001,130 A | 12/1999 | Bryan et al. |
| 6,033,438 A | 3/2000 | Bianchi et al. |
| 6,039,762 A | 3/2000 | McKay |
| 6,045,579 A | 4/2000 | Hochshuler et al. |
| 6,059,787 A | 5/2000 | Allen |
| 6,059,829 A | 5/2000 | Schlapfer et al. |
| 6,063,121 A | 5/2000 | Xavier et al. |
| 6,066,174 A | 5/2000 | Farris |
| 6,066,175 A | 5/2000 | Henderson et al. |
| 6,080,158 A | 6/2000 | Lin |
| 6,080,193 A | 6/2000 | Hochshuler et al. |
| 6,093,205 A | 7/2000 | Mcleod et al. |
| 6,096,038 A | 8/2000 | Michelson |
| 6,096,080 A | 8/2000 | Nicholson et al. |
| 6,099,531 A | 8/2000 | Bonutti |
| 6,102,950 A | 8/2000 | Vaccaro |
| 6,111,164 A | 8/2000 | Rainey et al. |
| 6,113,637 A | 9/2000 | Gill et al. |
| 6,113,638 A | 9/2000 | Williams et al. |
| 6,120,502 A | 9/2000 | Michelson |
| 6,123,705 A | 9/2000 | Michelson |
| 6,129,763 A | 10/2000 | Chauvin et al. |
| 6,136,031 A | 10/2000 | Middleton |
| 6,143,032 A | 11/2000 | Schafer et al. |
| 6,146,421 A | 11/2000 | Gordon et al. |
| 6,149,650 A | 11/2000 | Michelson |
| 6,156,067 A | 12/2000 | Bryan et al. |
| 6,174,311 B1 | 1/2001 | Branch et al. |
| 6,179,873 B1 | 1/2001 | Zientek |
| 6,179,875 B1 | 1/2001 | Von Strempel |
| 6,183,474 B1 | 2/2001 | Bramlet et al. |
| 6,193,757 B1 | 2/2001 | Foley et al. |
| 6,206,922 B1 | 3/2001 | Zdeblick et al. |
| 6,206,923 B1 | 3/2001 | Boyd et al. |
| 6,210,412 B1 | 4/2001 | Michelson |
| 6,210,442 B1 | 4/2001 | Wing et al. |
| 6,214,050 B1 | 4/2001 | Huene |
| 6,224,595 B1 | 5/2001 | Michelson |
| 6,231,610 B1 | 5/2001 | Geisler |
| 6,235,059 B1 | 5/2001 | Benezech et al. |
| 6,241,733 B1 | 6/2001 | Nicholson et al. |
| 6,241,769 B1 | 6/2001 | Nicholson et al. |
| 6,241,770 B1 | 6/2001 | Michelson |
| 6,241,771 B1 | 6/2001 | Gresser et al. |
| 6,245,072 B1 | 6/2001 | Zdeblick et al. |
| 6,245,108 B1 | 6/2001 | Biscup |
| 6,251,140 B1 | 6/2001 | Marino et al. |
| 6,258,089 B1 | 7/2001 | Campbell et al. |
| 6,258,094 B1 | 7/2001 | Nicholson et al. |
| 6,258,125 B1 | 7/2001 | Paul et al. |
| 6,261,293 B1 | 7/2001 | Nicholson et al. |
| 6,261,295 B1 | 7/2001 | Nicholson et al. |
| 6,264,656 B1 | 7/2001 | Michelson |
| 6,267,764 B1 | 7/2001 | Elberg |
| 6,270,498 B1 | 8/2001 | Michelson et al. |
| 6,277,149 B1 | 8/2001 | Boyle et al. |
| 6,296,664 B1 | 10/2001 | Middleton |
| 6,302,914 B1 | 10/2001 | Michelson |
| 6,306,170 B2 | 10/2001 | Ray |
| 6,315,797 B1 | 11/2001 | Middleton |
| 6,342,074 B1 | 1/2002 | Simpson |
| 6,348,071 B1 | 2/2002 | Steffee et al. |
| 6,350,283 B1 | 2/2002 | Michelson |
| 6,364,880 B1 | 4/2002 | Michelson |
| 6,371,987 B1 | 4/2002 | Weiland et al. |
| 6,371,988 B1 | 4/2002 | Pafford et al. |
| 6,375,655 B1 | 4/2002 | Zdeblick et al. |
| 6,383,186 B1 | 5/2002 | Michelson |
| 6,395,031 B1 | 5/2002 | Foley et al. |
| 6,395,035 B2 | 5/2002 | Bresina et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,419,703 B1 | 7/2002 | Fallin et al. |
| 6,419,704 B1 | 7/2002 | Ferree |
| 6,423,063 B1 | 7/2002 | Bonutti |
| 6,423,095 B1 | 7/2002 | Van Hoeck et al. |
| 6,432,106 B1 | 8/2002 | Fraser |
| 6,432,107 B1 | 8/2002 | Ferree |
| 6,447,512 B1 | 9/2002 | Landry et al. |
| 6,447,544 B1 | 9/2002 | Michelson |
| 6,447,546 B1 | 9/2002 | Bramlet et al. |
| 6,447,547 B1 | 9/2002 | Michelson |
| 6,454,769 B2 | 9/2002 | Wagner et al. |
| 6,458,159 B1 | 10/2002 | Thalgott |
| 6,461,359 B1 | 10/2002 | Tribus |
| 6,468,310 B1 | 10/2002 | Ralph et al. |
| 6,471,724 B2 | 10/2002 | Zdeblick et al. |
| 6,478,823 B1 | 11/2002 | Michelson |
| 6,482,233 B1 | 11/2002 | Aebi et al. |
| 6,482,584 B1 | 11/2002 | Mills et al. |
| 6,485,517 B1 | 11/2002 | Michelson |
| 6,497,726 B1 | 12/2002 | Carter et al. |
| 6,500,205 B1 | 12/2002 | Michelson |
| 6,524,312 B2 | 2/2003 | Landry et al. |
| 6,527,803 B1 | 3/2003 | Crozet et al. |
| 6,527,806 B2 | 3/2003 | Ralph et al. |
| 6,540,753 B2 | 4/2003 | Cohen |
| 6,540,785 B1 | 4/2003 | Gill et al. |
| 6,554,863 B2 | 4/2003 | Paul et al. |
| 6,558,423 B1 | 5/2003 | Michelson |
| 6,558,424 B2 | 5/2003 | Thalgott |
| 6,565,605 B2 | 5/2003 | Goble et al. |
| 6,576,016 B1 | 6/2003 | Hochshuler et al. |
| 6,579,291 B1 | 6/2003 | Keith et al. |
| 6,582,468 B1 | 6/2003 | Gauchet |
| 6,592,624 B1 | 7/2003 | Fraser et al. |
| 6,599,320 B1 | 7/2003 | Kuslich |
| 6,605,089 B1 | 8/2003 | Michelson |
| 6,607,530 B1 | 8/2003 | Carl et al. |
| 6,610,065 B1 | 8/2003 | Branch et al. |
| 6,610,089 B1 | 8/2003 | Liu et al. |
| 6,610,092 B2 | 8/2003 | Ralph et al. |
| 6,613,091 B1 | 9/2003 | Zdeblick et al. |
| 6,613,278 B1 | 9/2003 | Mills et al. |
| 6,616,671 B2 | 9/2003 | Landry et al. |
| 6,620,163 B1 | 9/2003 | Michelson |
| 6,635,086 B2 | 10/2003 | Lin |

(56) References Cited

U.S. PATENT DOCUMENTS

| | | |
|---|---|---|
| 6,635,087 B2 | 10/2003 | Angelucci et al. |
| 6,645,206 B1 | 11/2003 | Zdeblick et al. |
| 6,645,249 B2 | 11/2003 | Ralph et al. |
| 6,648,893 B2 | 11/2003 | Dudasik |
| 6,652,584 B2 | 11/2003 | Michelson |
| 6,652,818 B1 | 11/2003 | Mills et al. |
| 6,660,038 B2 | 12/2003 | Boyer, II et al. |
| 6,666,890 B2 | 12/2003 | Michelson |
| 6,669,730 B2 | 12/2003 | Ralph et al. |
| 6,669,731 B2 | 12/2003 | Ralph et al. |
| 6,673,113 B2 | 1/2004 | Ralph et al. |
| 6,676,703 B2 | 1/2004 | Biscup |
| 6,679,887 B2 | 1/2004 | Nicholson et al. |
| 6,679,915 B1 | 1/2004 | Cauthen |
| 6,695,846 B2 | 2/2004 | Richelsoph et al. |
| 6,695,851 B2 | 2/2004 | Zdeblick et al. |
| 6,695,882 B2 | 2/2004 | Bianchi et al. |
| 6,706,067 B2 | 3/2004 | Shimp et al. |
| 6,709,458 B2 | 3/2004 | Michelson |
| 6,712,818 B1 | 3/2004 | Michelson |
| 6,716,247 B2 | 4/2004 | Michelson |
| 6,719,794 B2 | 4/2004 | Gerber et al. |
| 6,723,128 B2 | 4/2004 | Uk |
| 6,733,504 B2 | 5/2004 | Lin et al. |
| 6,733,531 B1 | 5/2004 | Trieu |
| 6,733,535 B2 | 5/2004 | Michelson |
| 6,736,850 B2 | 5/2004 | Davis |
| 6,740,117 B2 | 5/2004 | Ralph et al. |
| 6,740,118 B2 | 5/2004 | Eisermann et al. |
| 6,743,255 B2 | 6/2004 | Ferree |
| 6,743,256 B2 | 6/2004 | Mason |
| 6,743,257 B2 | 6/2004 | Castro |
| 6,749,636 B2 | 6/2004 | Michelson |
| 6,758,849 B1 | 7/2004 | Michelson |
| 6,767,367 B1 | 7/2004 | Michelson |
| 6,770,074 B2 | 8/2004 | Michelson |
| 6,770,096 B2 | 8/2004 | Bolger et al. |
| 6,793,679 B2 | 9/2004 | Michelson |
| RE38,614 E | 10/2004 | Paul et al. |
| 6,800,092 B1 | 10/2004 | Williams et al. |
| 6,800,093 B2 | 10/2004 | Nicholson et al. |
| 6,805,713 B1 | 10/2004 | Carter et al. |
| 6,805,714 B2 | 10/2004 | Sutcliffe |
| 6,808,537 B2 | 10/2004 | Michelson |
| 6,835,206 B2 | 12/2004 | Jackson |
| 6,849,093 B2 | 2/2005 | Michelson |
| 6,890,355 B2 | 5/2005 | Michelson |
| 6,902,580 B2 | 6/2005 | Fallin et al. |
| 6,923,811 B1 | 8/2005 | Carl et al. |
| 6,923,830 B2 | 8/2005 | Michelson |
| 6,955,691 B2 | 10/2005 | Chae et al. |
| 6,962,606 B2 | 11/2005 | Michelson |
| 6,964,687 B1 | 11/2005 | Bernard et al. |
| 6,972,019 B2 | 12/2005 | Michelson |
| 6,972,035 B2 | 12/2005 | Michelson |
| 6,981,975 B2 | 1/2006 | Michelson |
| 6,984,234 B2 | 1/2006 | Bray |
| 6,994,727 B2 | 2/2006 | Khandkar et al. |
| 7,001,385 B2 | 2/2006 | Bonutti |
| 7,008,453 B1 | 3/2006 | Michelson |
| 7,018,412 B2 | 3/2006 | Ferreira et al. |
| 7,033,394 B2 | 4/2006 | Michelson |
| 7,041,135 B2 | 5/2006 | Michelson |
| 7,041,136 B2 | 5/2006 | Goble et al. |
| 7,048,762 B1 | 5/2006 | Sander et al. |
| 7,048,765 B1 | 5/2006 | Grooms et al. |
| 7,051,610 B2 | 5/2006 | Stoianovici et al. |
| 7,060,097 B2 | 6/2006 | Fraser et al. |
| 7,063,701 B2 | 6/2006 | Michelson |
| 7,063,702 B2 | 6/2006 | Michelson |
| 7,066,961 B2 | 6/2006 | Michelson |
| 7,074,237 B2 | 7/2006 | Goble et al. |
| 7,090,698 B2 | 8/2006 | Goble et al. |
| 7,094,239 B1 | 8/2006 | Michelson |
| 7,112,206 B2 | 9/2006 | Michelson |
| 7,118,579 B2 | 10/2006 | Michelson |
| 7,118,598 B2 | 10/2006 | Michelson |
| 7,128,760 B2 | 10/2006 | Michelson |
| 7,128,761 B2 | 10/2006 | Kuras et al. |
| 7,137,984 B2 | 11/2006 | Michelson |
| 7,153,325 B2 | 12/2006 | Kim et al. |
| 7,163,561 B2 | 1/2007 | Michelson |
| 7,172,627 B2 | 2/2007 | Fiere et al. |
| 7,211,112 B2 | 5/2007 | Baynham et |
| 7,217,291 B2 | 5/2007 | Zucherman et al. |
| 7,217,293 B2 | 5/2007 | Branch |
| 7,223,289 B2 | 5/2007 | Trieu et al. |
| 7,232,463 B2 | 6/2007 | Falahee |
| 7,232,464 B2 | 6/2007 | Mathieu et al. |
| 7,235,082 B2 | 6/2007 | Bartish et al. |
| 7,255,698 B2 | 8/2007 | Michelson |
| 7,276,081 B1 | 10/2007 | Coates et al. |
| 7,291,170 B2 | 11/2007 | Huppert |
| 7,303,583 B1 | 12/2007 | Schär et al. |
| 7,326,248 B2 | 2/2008 | Michelson |
| 7,361,196 B2 | 4/2008 | Fallin et al. |
| 7,410,501 B2 | 8/2008 | Michelson |
| 7,431,735 B2 | 10/2008 | Liu et al. |
| 7,435,262 B2 | 10/2008 | Michelson |
| 7,442,209 B2 | 10/2008 | Michelson |
| 7,445,636 B2 | 10/2008 | Liu et al. |
| 7,445,635 B2 | 11/2008 | Fallin et al. |
| 7,455,684 B2 | 11/2008 | Gradel et al. |
| 7,455,692 B2 | 11/2008 | Michelson |
| 7,465,317 B2 | 12/2008 | Malberg et al. |
| 7,470,273 B2 * | 12/2008 | Dougherty-Shah ............... A61F 2/4611 606/86 A |
| 7,473,276 B2 | 1/2009 | Aebi et al. |
| 7,479,160 B2 | 1/2009 | Branch et al. |
| 7,503,933 B2 | 3/2009 | Michelson |
| 7,540,882 B2 | 6/2009 | Michelson |
| 7,563,284 B2 | 7/2009 | Coppes et al. |
| 7,563,286 B2 | 7/2009 | Gerber et al. |
| 7,566,345 B1 | 7/2009 | Fallin et al. |
| 7,588,590 B2 | 9/2009 | Chervitz et al. |
| 7,591,851 B2 | 9/2009 | Winslow et al. |
| 7,594,931 B2 | 9/2009 | Louis et al. |
| 7,594,932 B2 | 9/2009 | Aferzon et al. |
| 7,601,170 B2 | 10/2009 | Winslow et al. |
| 7,604,654 B2 | 10/2009 | Fallin et al. |
| 7,608,107 B2 | 10/2009 | Michelson |
| 7,611,538 B2 | 11/2009 | Belliard et al. |
| 7,618,453 B2 | 11/2009 | Goble et al. |
| 7,618,455 B2 | 11/2009 | Goble et al. |
| 7,618,456 B2 | 11/2009 | Mathieu et al. |
| 7,621,955 B2 | 11/2009 | Goble et al. |
| 7,621,958 B2 | 11/2009 | Zdeblick et al. |
| 7,625,393 B2 | 12/2009 | Fallin et al. |
| 7,637,951 B2 | 12/2009 | Michelson |
| 7,637,953 B2 | 12/2009 | Branch et al. |
| 7,637,954 B2 | 12/2009 | Michelson |
| 7,641,690 B2 | 1/2010 | Abdou |
| 7,655,027 B2 | 2/2010 | Michelson |
| 7,658,766 B2 | 2/2010 | Melkent et al. |
| 7,682,396 B2 | 3/2010 | Beaurain et al. |
| 7,695,516 B2 | 4/2010 | Zeegers |
| 7,695,517 B2 | 4/2010 | Benzel et al. |
| 7,727,280 B2 | 6/2010 | McLuen |
| 7,744,602 B2 | 6/2010 | Teeny et al. |
| 7,749,252 B2 | 7/2010 | Zucherman et al. |
| 7,749,274 B2 | 7/2010 | Razian |
| 7,753,937 B2 | 7/2010 | Chervitz et al. |
| 7,771,473 B2 | 8/2010 | Thramann |
| 7,771,475 B2 | 8/2010 | Michelson |
| 7,776,090 B2 | 8/2010 | Winslow et al. |
| 7,780,670 B2 | 8/2010 | Bonutti |
| 7,789,914 B2 | 9/2010 | Michelson |
| 7,794,502 B2 | 9/2010 | Michelson |
| 7,799,053 B2 | 9/2010 | Haid, Jr. et al. |
| 7,799,057 B2 | 9/2010 | Hudgins et al. |
| 7,799,081 B2 | 9/2010 | McKinley |
| 7,811,326 B2 | 10/2010 | Braddock, Jr. et al. |
| 7,819,903 B2 | 10/2010 | Fraser et al. |

(56) References Cited

U.S. PATENT DOCUMENTS

| | | |
|---|---|---|
| 7,824,445 B2 | 11/2010 | Biro et al. |
| 7,833,255 B2 | 11/2010 | Chow et al. |
| 7,842,088 B2 | 11/2010 | Rashbaum et al. |
| 7,846,188 B2 | 12/2010 | Moskowitz et al. |
| 7,846,207 B2 | 12/2010 | Lechmann et al. |
| 7,850,731 B2 | 12/2010 | Brittan et al. |
| 7,850,732 B2 | 12/2010 | Heinz |
| 7,850,733 B2 | 12/2010 | Baynham et al. |
| 7,862,616 B2 | 1/2011 | Lechmann et al. |
| 7,871,441 B2 | 1/2011 | Eckman |
| 7,875,076 B2 | 1/2011 | Mathieu et al. |
| 7,887,591 B2 | 2/2011 | Aebi et al. |
| 7,892,261 B2 | 2/2011 | Bonutti |
| 7,892,286 B2 | 2/2011 | Michelson |
| 7,905,886 B1 | 3/2011 | Curran et al. |
| 7,909,871 B2 | 3/2011 | Abdou |
| 7,914,560 B2 | 3/2011 | Hoy et al. |
| 7,922,729 B2 | 4/2011 | Michelson |
| 7,931,674 B2 | 4/2011 | Zucherman et al. |
| 7,931,840 B2 | 4/2011 | Michelson |
| 7,935,149 B2 | 5/2011 | Michelson |
| 7,951,198 B2 | 5/2011 | Sucec et al. |
| 7,955,390 B2 | 6/2011 | Fallin et al. |
| 7,972,337 B2 | 7/2011 | Boyajian et al. |
| 7,972,363 B2 | 7/2011 | Moskowitz et al. |
| 7,972,365 B2 | 7/2011 | Michelson |
| 7,976,566 B2 | 7/2011 | Michelson |
| 7,985,255 B2 | 7/2011 | Bray et al. |
| 7,985,258 B2 | 7/2011 | Zdeblick et al. |
| 7,993,373 B2 | 8/2011 | Hoy et al. |
| 7,998,177 B2 | 8/2011 | Hoy et al. |
| 7,998,178 B2 | 8/2011 | Hoy et al. |
| 7,998,211 B2 | 8/2011 | Baccelli et al. |
| 8,007,534 B2 | 8/2011 | Michelson |
| 8,021,401 B2 | 9/2011 | Carl et al. |
| 8,021,430 B2 | 9/2011 | Michelson |
| 8,043,334 B2 | 10/2011 | Fisher et al. |
| 8,062,336 B2 | 11/2011 | Triplett et al. |
| 8,062,375 B2 | 11/2011 | Glerum et al. |
| 8,066,741 B2 | 11/2011 | Fallin et al. |
| 8,066,749 B2 | 11/2011 | Winslow et al. |
| 8,070,816 B2 | 12/2011 | Taylor |
| 8,070,819 B2 | 12/2011 | Aferzon et al. |
| 8,075,593 B2 | 12/2011 | Hess |
| 8,075,618 B2 | 12/2011 | Trieu et al. |
| 8,075,621 B2 | 12/2011 | Michelson |
| 8,080,062 B2 | 12/2011 | Armstrong et al. |
| 8,097,034 B2 | 1/2012 | Michelson |
| 8,114,082 B2 | 2/2012 | Boyajian et al. |
| 8,118,873 B2 | 2/2012 | Humphreys et al. |
| 8,137,405 B2 | 3/2012 | Kostuik et al. |
| 8,147,556 B2 | 4/2012 | Louis et al. |
| 8,167,946 B2 | 5/2012 | Michelson |
| 8,167,949 B2 | 5/2012 | Tyber et al. |
| 8,167,950 B2 | 5/2012 | Aferzon et al. |
| 8,182,539 B2 | 5/2012 | Tyber et al. |
| 8,187,329 B2 | 5/2012 | Theofilos |
| 8,187,332 B2 | 5/2012 | Mcluen |
| 8,216,312 B2 | 7/2012 | Gray |
| 8,221,422 B2 | 7/2012 | Mangione |
| 8,241,359 B2 | 8/2012 | Davis et al. |
| 8,257,443 B2 | 9/2012 | Kamran et al. |
| 8,262,700 B2 | 9/2012 | Cho et al. |
| 8,267,999 B2 | 9/2012 | Beaurain et al. |
| 8,303,663 B2 | 11/2012 | Jimenez et al. |
| 8,313,528 B1 | 11/2012 | Wensel |
| 8,323,345 B2 | 12/2012 | Sledge |
| 8,343,197 B2 | 1/2013 | Gonzalez-Hernandez |
| 8,343,219 B2 | 1/2013 | Allain et al. |
| 8,349,015 B2 | 1/2013 | Bae et al. |
| 8,409,288 B2 | 4/2013 | Davis et al. |
| 8,535,352 B2 | 9/2013 | Altarac et al. |
| 8,545,563 B2 | 10/2013 | Brun et al. |
| 8,617,245 B2 | 12/2013 | Brett |
| 8,696,681 B2 | 4/2014 | Harris et al. |
| 9,044,337 B2 | 6/2015 | Dinville et al. |
| 9,566,164 B2 | 2/2017 | Zeegers |
| 9,597,198 B2 | 3/2017 | Davis et al. |
| 9,713,535 B2 | 7/2017 | Davis et al. |
| 9,763,803 B2 | 9/2017 | Dinville et al. |
| 2001/0018614 A1 | 8/2001 | Bianchi |
| 2001/0020185 A1 | 9/2001 | Ray |
| 2001/0031254 A1 | 10/2001 | Bianchi et al. |
| 2001/0031967 A1 | 10/2001 | Nicholson et al. |
| 2002/0016592 A1 | 2/2002 | Branch et al. |
| 2002/0026243 A1 | 2/2002 | Lin |
| 2002/0032483 A1 | 3/2002 | Nicholson et al. |
| 2002/0040243 A1 | 4/2002 | Attali et al. |
| 2002/0059938 A1 | 5/2002 | Fogarty et al. |
| 2002/0070565 A1 | 6/2002 | Szapucki et al. |
| 2002/0072806 A1 | 6/2002 | Buskirk et al. |
| 2002/0082597 A1 | 6/2002 | Fraser |
| 2002/0082700 A1 | 6/2002 | Bianchi et al. |
| 2002/0087212 A1 | 7/2002 | James et al. |
| 2002/0106393 A1 | 8/2002 | Bianchi et al. |
| 2002/0107572 A1 | 8/2002 | Foley et al. |
| 2002/0119437 A1 | 8/2002 | Grroms et al. |
| 2002/0138143 A1 | 9/2002 | Grooms et al. |
| 2002/0151893 A1 | 10/2002 | Santilli |
| 2002/0161444 A1 | 10/2002 | Choi |
| 2002/0165612 A1 | 11/2002 | Gerber et al. |
| 2002/0165613 A1 | 11/2002 | Lin et al. |
| 2002/0193880 A1 | 12/2002 | Fraser |
| 2003/0023304 A1 | 1/2003 | Carter et al. |
| 2003/0027125 A1 | 2/2003 | Mills et al. |
| 2003/0028249 A1 | 2/2003 | Baccelli et al. |
| 2003/0060886 A1 | 3/2003 | Van Hoeck et al. |
| 2003/0069640 A1 | 4/2003 | Ferreira et al. |
| 2003/0074075 A1 | 4/2003 | Thomas, Jr. et al. |
| 2003/0097179 A1 | 5/2003 | Carter et al. |
| 2003/0100950 A1 | 5/2003 | Moret |
| 2003/0109928 A1 | 6/2003 | Pasquet et al. |
| 2003/0135279 A1 | 7/2003 | Michelson |
| 2003/0139815 A1 | 7/2003 | Grooms et al. |
| 2003/0149438 A1 | 8/2003 | Nichols et al. |
| 2003/0149484 A1 | 8/2003 | Michelson |
| 2003/0167091 A1 | 9/2003 | Scharf |
| 2003/0187436 A1 | 10/2003 | Bolger et al. |
| 2003/0191531 A1 | 10/2003 | Berry et al. |
| 2003/0195514 A1 | 10/2003 | Trieu et al. |
| 2003/0195626 A1 | 10/2003 | Huppert |
| 2003/0195629 A1 | 10/2003 | Pafford et al. |
| 2003/0195632 A1 | 10/2003 | Foley et al. |
| 2003/0204260 A1 | 10/2003 | Ferree |
| 2003/0233147 A1 | 12/2003 | Nicholson et al. |
| 2004/0010312 A1 | 1/2004 | Enayati |
| 2004/0030387 A1 | 2/2004 | Landry et al. |
| 2004/0073307 A1 | 4/2004 | Keller |
| 2004/0073309 A1 | 4/2004 | Bianchi et al. |
| 2004/0073313 A1 | 4/2004 | Link et al. |
| 2004/0093083 A1 | 5/2004 | Branch et al. |
| 2004/0097929 A1 | 5/2004 | Branch et al. |
| 2004/0115172 A1 | 6/2004 | Bianchi et al. |
| 2004/0117022 A1 | 6/2004 | Marnay et al. |
| 2004/0127990 A1 | 7/2004 | Charles, Jr. et al. |
| 2004/0127993 A1 | 7/2004 | Kast et al. |
| 2004/0127994 A1 | 7/2004 | Kast et al. |
| 2004/0148029 A1 | 7/2004 | Bianchi et al. |
| 2004/0162617 A1 | 8/2004 | Zucherman et al. |
| 2004/0172020 A1 | 9/2004 | Beaurain et al. |
| 2004/0172130 A1 | 9/2004 | Nakahara et al. |
| 2004/0199254 A1 | 10/2004 | Louis et al. |
| 2004/0210219 A1 | 10/2004 | Bray |
| 2004/0210227 A1 | 10/2004 | Trail et al. |
| 2004/0210308 A1 | 10/2004 | Carter et al. |
| 2004/0210313 A1 | 10/2004 | Michelson |
| 2004/0230306 A1 | 11/2004 | Hoeck et al. |
| 2004/0243238 A1 | 12/2004 | Arnin et al. |
| 2004/0243240 A1 | 12/2004 | Beaurain et al. |
| 2004/0254577 A1 | 12/2004 | Delecrin et al. |
| 2004/0254643 A1 | 12/2004 | Jackson |
| 2005/0004672 A1 | 1/2005 | Pafford et al. |
| 2005/0010215 A1 | 1/2005 | Delecrin et al. |
| 2005/0015149 A1 | 1/2005 | Michelson |

(56) References Cited

U.S. PATENT DOCUMENTS

| | | |
|---|---|---|
| 2005/0027359 A1 | 2/2005 | Mashburn |
| 2005/0027360 A1 | 2/2005 | Webb et al. |
| 2005/0027362 A1 | 2/2005 | Williams et al. |
| 2005/0038511 A1 | 2/2005 | Martz et al. |
| 2005/0038512 A1 | 2/2005 | Michelson |
| 2005/0049590 A1 | 3/2005 | Alleyne et al. |
| 2005/0060034 A1 | 3/2005 | Berry et al. |
| 2005/0060037 A1 | 3/2005 | Michelson |
| 2005/0065608 A1 | 3/2005 | Michelson |
| 2005/0065611 A1 | 3/2005 | Huppert et al. |
| 2005/0085917 A1 | 4/2005 | Marnay et al. |
| 2005/0096742 A1 | 5/2005 | Mills et al. |
| 2005/0096745 A1 | 5/2005 | Andre et al. |
| 2005/0100862 A1 | 5/2005 | Mills et al. |
| 2005/0101957 A1 | 5/2005 | Buskirk et al. |
| 2005/0107788 A1 | 5/2005 | Beaurain et al. |
| 2005/0119744 A1 | 6/2005 | Buskirk et al. |
| 2005/0119747 A1 | 6/2005 | Fabris Monterumici et al. |
| 2005/0143733 A1 | 6/2005 | Petit |
| 2005/0143825 A1 | 6/2005 | Enayati |
| 2005/0149189 A1 | 7/2005 | Mokhtar et al. |
| 2005/0165483 A1 | 7/2005 | Ray, III et al. |
| 2005/0171554 A1 | 8/2005 | Estes et al. |
| 2005/0177236 A1 | 8/2005 | Mathieu et al. |
| 2005/0197706 A1 | 9/2005 | Hovorka et al. |
| 2005/0246024 A1 | 11/2005 | Zeegers |
| 2005/0283236 A1 | 12/2005 | Razian |
| 2005/0288788 A1 | 12/2005 | Dougherty-shah |
| 2006/0058878 A1 | 3/2006 | Michelson |
| 2006/0069437 A1 | 3/2006 | Weber |
| 2006/0085071 A1 | 4/2006 | Lechmann et al. |
| 2006/0085076 A1 | 4/2006 | Krishna et al. |
| 2006/0089717 A1 | 4/2006 | Krishna et al. |
| 2006/0095136 A1 | 5/2006 | Mcluen |
| 2006/0121084 A1 | 6/2006 | Borden et al. |
| 2006/0122703 A1 | 6/2006 | Aebi et al. |
| 2006/0129244 A1 | 6/2006 | Ensign |
| 2006/0136063 A1 | 6/2006 | Zeegers |
| 2006/0142863 A1 | 6/2006 | Fraser et al. |
| 2006/0155377 A1 | 7/2006 | Beaurain et al. |
| 2006/0173544 A1 | 8/2006 | Gau |
| 2006/0186063 A1 | 8/2006 | Campbell |
| 2006/0206208 A1 | 9/2006 | Michelson |
| 2006/0235426 A1 | 10/2006 | Lim et al. |
| 2006/0241621 A1 | 10/2006 | Moskowitz et al. |
| 2006/0241761 A1* | 10/2006 | Gately .................. A61F 2/4465 623/17.11 |
| 2006/0241764 A1 | 10/2006 | Michelson |
| 2006/0253201 A1 | 11/2006 | Mcluen |
| 2006/0276899 A1 | 12/2006 | Zipnick et al. |
| 2006/0282074 A1 | 12/2006 | Renaud et al. |
| 2007/0016217 A1 | 1/2007 | Dinville |
| 2007/0016297 A1 | 1/2007 | Johnson |
| 2007/0032871 A1 | 2/2007 | Michelson |
| 2007/0049943 A1 | 3/2007 | Moskowitz et al. |
| 2007/0073404 A1 | 3/2007 | Rashbaum et al. |
| 2007/0093850 A1* | 4/2007 | Harris .................... H05B 47/16 606/99 |
| 2007/0106388 A1 | 5/2007 | Michelson |
| 2007/0142843 A1 | 6/2007 | Dye |
| 2007/0162128 A1 | 7/2007 | DeRidder et al. |
| 2007/0162130 A1 | 7/2007 | Rashbaum et al. |
| 2007/0179623 A1 | 8/2007 | Trieu et al. |
| 2007/0208345 A1 | 9/2007 | Marnay et al. |
| 2007/0233253 A1 | 10/2007 | Bray et al. |
| 2007/0250167 A1 | 10/2007 | Bray et al. |
| 2007/0260249 A1 | 11/2007 | Boyajian et al. |
| 2007/0270951 A1 | 11/2007 | Davis et al. |
| 2007/0270954 A1 | 11/2007 | Wu |
| 2007/0270960 A1 | 11/2007 | Bonin, Jr. et al. |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2008/0021562 A1 | 1/2008 | Huppert |
| 2008/0027547 A1 | 1/2008 | Yu et al. |
| 2008/0027550 A1 | 1/2008 | Link et al. |
| 2008/0033432 A1 | 2/2008 | Mcgraw et al. |
| 2008/0033562 A1 | 2/2008 | Krishna et al. |
| 2008/0051887 A1 | 2/2008 | Carter et al. |
| 2008/0109083 A1 | 5/2008 | Van Hoeck et al. |
| 2008/0125865 A1 | 5/2008 | Abdelgany |
| 2008/0132949 A1 | 6/2008 | Aferzon et al. |
| 2008/0161933 A1 | 7/2008 | Grotz et al. |
| 2008/0177306 A1 | 7/2008 | Lamborne et al. |
| 2008/0195211 A1 | 8/2008 | Lin et al. |
| 2008/0200984 A1 | 8/2008 | Jodaitis et al. |
| 2008/0234686 A1 | 9/2008 | Beaurain et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0255617 A1 | 10/2008 | Cho et al. |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2008/0312743 A1 | 12/2008 | Villa et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0099601 A1 | 4/2009 | Aferzon et al. |
| 2009/0099604 A1 | 4/2009 | Cho et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0112271 A1 | 4/2009 | Moskowitz et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0157188 A1 | 6/2009 | Zeegers |
| 2009/0164020 A1 | 6/2009 | Janowski et al. |
| 2009/0182381 A1 | 7/2009 | Beaurain et al. |
| 2009/0182429 A1 | 7/2009 | Humphreys et al. |
| 2009/0182430 A1 | 7/2009 | Tyber et al. |
| 2009/0186333 A1 | 7/2009 | Mills et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216241 A1 | 8/2009 | Dinville |
| 2009/0216331 A1 | 8/2009 | Grotz et al. |
| 2009/0222092 A1 | 9/2009 | Davis et al. |
| 2009/0222100 A1 | 9/2009 | Cipoletti et al. |
| 2009/0234455 A1 | 9/2009 | Moskowitz et al. |
| 2009/0265007 A1 | 10/2009 | Colleran |
| 2009/0270990 A1 | 10/2009 | Louis et al. |
| 2010/0004664 A1 | 1/2010 | Boyajian et al. |
| 2010/0010547 A1 | 1/2010 | Beaurain et al. |
| 2010/0016903 A1 | 1/2010 | Matityahu et al. |
| 2010/0016974 A1 | 1/2010 | Janowski et al. |
| 2010/0049259 A1 | 2/2010 | Lambrecht et al. |
| 2010/0050276 A1 | 2/2010 | Depaepe |
| 2010/0057206 A1 | 3/2010 | Duffield et al. |
| 2010/0057207 A1 | 3/2010 | Ray, III et al. |
| 2010/0063554 A1 | 3/2010 | Branch et al. |
| 2010/0070037 A1 | 3/2010 | Parry et al. |
| 2010/0082104 A1 | 4/2010 | Carter et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0145459 A1 | 6/2010 | Mcdonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |

(56) References Cited

U.S. PATENT DOCUMENTS

| | | |
|---|---|---|
| 2010/0217396 A1 | 8/2010 | Bianchi et al. |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0268349 A1 | 10/2010 | Bianchi et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0298941 A1 | 11/2010 | Hes et al. |
| 2010/0305700 A1 | 12/2010 | Ben-Arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0098747 A1 | 4/2011 | Donner et al. |
| 2011/0112587 A1 | 5/2011 | Patel et al. |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |
| 2011/0166655 A1 | 7/2011 | Michelson |
| 2011/0166656 A1 | 7/2011 | Thalgott et al. |
| 2011/0166657 A1 | 7/2011 | Thalgott et al. |
| 2011/0166658 A1 | 7/2011 | Garber et al. |
| 2011/0172774 A1 | 7/2011 | Varela |
| 2011/0178599 A1 | 7/2011 | Brett |
| 2011/0196492 A1 | 8/2011 | Lambrecht et al. |
| 2011/0196493 A1 | 8/2011 | Pimenta |
| 2011/0196494 A1 | 8/2011 | Yedlicka et al. |
| 2011/0202136 A1 | 8/2011 | Brittan et al. |
| 2011/0208311 A1 | 8/2011 | Janowski |
| 2011/0208313 A1 | 8/2011 | Michelson |
| 2011/0230969 A1 | 9/2011 | Biedermann et al. |
| 2011/0230971 A1 | 9/2011 | Donner et al. |
| 2011/0264227 A1 | 10/2011 | Boyajian et al. |
| 2011/0295371 A1 | 12/2011 | Moskowitz et al. |
| 2011/0301707 A1 | 12/2011 | Buskirk et al. |
| 2011/0301713 A1 | 12/2011 | Theofilos |
| 2011/0301714 A1 | 12/2011 | Theofilos |
| 2011/0313528 A1 | 12/2011 | Laubert et al. |
| 2012/0004660 A1 | 1/2012 | Grooms et al. |
| 2012/0022654 A1 | 1/2012 | Farris et al. |
| 2012/0053693 A1 | 3/2012 | Zeegers |
| 2012/0078371 A1 | 3/2012 | Gamache et al. |
| 2012/0116466 A1 | 5/2012 | Dinville et al. |
| 2012/0191196 A1 | 7/2012 | Louis et al. |
| 2012/0197404 A1 | 8/2012 | Brun et al. |
| 2012/0265248 A1 | 10/2012 | Delecrin et al. |
| 2012/0310356 A1 | 12/2012 | Davis et al. |
| 2012/0330424 A1 | 12/2012 | Zeegers |
| 2013/0013006 A1 | 1/2013 | Rashbaum et al. |
| 2013/0041408 A1 | 2/2013 | Dinville et al. |
| 2013/0150968 A1 | 6/2013 | Dinville et al. |
| 2013/0166029 A1 | 6/2013 | Dinville et al. |
| 2013/0226300 A1 | 8/2013 | Chataigner et al. |
| 2013/0253648 A1 | 9/2013 | Beaurain et al. |
| 2013/0253651 A1 | 9/2013 | Dinville |
| 2013/0282124 A1 | 10/2013 | Jodaitis et al. |
| 2014/0052262 A1 | 2/2014 | Brett |
| 2014/0114413 A1 | 4/2014 | Allain et al. |
| 2014/0121778 A1 | 5/2014 | Huppert |
| 2014/0135932 A1 | 5/2014 | Davis et al. |
| 2014/0135935 A1 | 5/2014 | Vila et al. |
| 2014/0148855 A1 | 5/2014 | Beaurain et al. |
| 2014/0214168 A1 | 7/2014 | Jodaitis et al. |
| 2014/0228885 A1 | 8/2014 | Dinville et al. |
| 2014/0316466 A1 | 10/2014 | Dinville et al. |
| 2014/0364949 A1 | 12/2014 | Beaurain et al. |
| 2015/0025638 A1 | 1/2015 | Rashbaum et al. |
| 2015/0032209 A1 | 1/2015 | Hovorka et al. |
| 2015/0045893 A1 | 2/2015 | Dinville et al. |
| 2015/0051702 A1 | 2/2015 | Chataigner et al. |
| 2015/0080959 A1 | 3/2015 | Renaud et al. |
| 2015/0127107 A1 | 5/2015 | Kim et al. |
| 2015/0127109 A1 | 5/2015 | Brett |
| 2015/0182259 A1 | 7/2015 | Cho et al. |
| 2015/0182264 A1 | 7/2015 | Delecrin et al. |
| 2015/0190240 A1 | 7/2015 | Rashbaum et al. |
| 2015/0209089 A1 | 7/2015 | Chataigner et al. |
| 2015/0245918 A1 | 9/2015 | Zeegers |
| 2015/0250605 A1 | 9/2015 | Chataigner et al. |
| 2015/0320568 A1 | 11/2015 | Ameil et al. |
| 2016/0008142 A1 | 1/2016 | Louis et al. |
| 2016/0051380 A1 | 2/2016 | Dinville et al. |
| 2016/0100870 A1 | 4/2016 | Lavigne et al. |
| 2016/0100953 A1 | 4/2016 | Dinville et al. |
| 2016/0166402 A1 | 6/2016 | Steib |
| 2016/0220389 A1 | 8/2016 | Dinville |
| 2016/0235547 A1 | 8/2016 | Beaurain et al. |
| 2016/0317190 A1 | 11/2016 | Beaurain et al. |
| 2016/0317195 A1 | 11/2016 | Dinville et al. |
| 2017/0042692 A1 | 2/2017 | Stewart et al. |
| 2017/0252183 A1 | 9/2017 | Davis et al. |
| 2017/0299525 A1 | 10/2017 | Cui et al. |

FOREIGN PATENT DOCUMENTS

| | | |
|---|---|---|
| DE | 4315757 C1 | 11/1994 |
| DE | 4318700 C1 | 11/1994 |
| DE | 4423826 A1 | 1/1995 |
| DE | 4328690 A1 | 3/1995 |
| DE | 4327054 C1 | 4/1995 |
| DE | 9413778 U1 | 1/1996 |
| DE | 19615938 A1 | 10/1996 |
| DE | 10323368 B3 | 8/2004 |
| DE | 20320454 U1 | 10/2004 |
| DE | 10323363 A1 | 12/2004 |
| EP | 0179695 A1 | 4/1986 |
| EP | 0298235 A1 | 1/1989 |
| EP | 0346129 A1 | 12/1989 |
| EP | 0356112 A1 | 2/1990 |
| EP | 0392076 A1 | 10/1990 |
| EP | 0538183 A1 | 4/1993 |
| EP | 0599419 A2 | 6/1994 |
| EP | 0630625 A2 | 12/1994 |
| EP | 0637439 A1 | 2/1995 |
| EP | 0637440 A1 | 2/1995 |
| EP | 0662309 A1 | 7/1995 |
| EP | 0667127 A1 | 8/1995 |
| EP | 0697200 A1 | 2/1996 |
| EP | 0951879 A2 | 10/1999 |
| EP | 0965313 A1 | 12/1999 |
| EP | 1996127 A2 | 12/2008 |
| EP | 2113228 A1 | 11/2009 |
| EP | 2327375 A1 | 6/2011 |
| EP | 2340788 A1 | 7/2011 |
| EP | 2363080 A1 | 9/2011 |
| FR | 2703580 A1 | 10/1994 |
| FR | 2710519 A1 | 4/1995 |
| FR | 2724312 A1 | 3/1996 |
| FR | 2733413 A1 | 10/1996 |
| FR | 2736537 A1 | 1/1997 |
| FR | 2747034 A1 | 10/1997 |
| FR | 2808995 A1 | 11/2001 |
| FR | 2823095 A1 | 10/2002 |
| FR | 2827156 A1 | 1/2003 |
| FR | 2846550 A1 | 5/2004 |
| FR | 2861582 A1 | 5/2005 |
| FR | 2879436 A1 | 6/2006 |
| FR | 2880795 A1 | 7/2006 |
| FR | 2891135 A1 | 3/2007 |
| FR | 2897259 A1 | 8/2007 |

(56) References Cited

FOREIGN PATENT DOCUMENTS

| | | |
|---|---|---|
| FR | 2916956 A1 | 12/2008 |
| FR | 2987256 A1 | 8/2013 |
| FR | 3005569 A1 | 11/2014 |
| FR | 3016793 A1 | 7/2015 |
| JP | 03505416 A | 11/1991 |
| JP | 06285099 A | 10/1994 |
| JP | 08503876 A | 4/1996 |
| JP | 09503416 A | 4/1997 |
| JP | 09122160 A | 5/1997 |
| JP | 11506658 A | 6/1999 |
| JP | 11513601 A | 11/1999 |
| JP | 2001507243 A | 6/2001 |
| PE | 19504867 C1 | 2/1996 |
| RU | 2004218 C1 | 12/1993 |
| RU | 2177278 C2 | 12/2001 |
| WO | WO-9011740 A1 | 10/1990 |
| WO | WO-9310725 A2 | 6/1993 |
| WO | WO-9507668 A1 | 3/1995 |
| WO | WO-9508306 A1 | 3/1995 |
| WO | WO-9617564 A1 | 6/1996 |
| WO | WO-9627348 A1 | 9/1996 |
| WO | WO-9640014 A1 | 12/1996 |
| WO | WO-9706753 A2 | 2/1997 |
| WO | WO-9715247 A1 | 5/1997 |
| WO | WO-9715248 A1 | 5/1997 |
| WO | WO-9723175 A1 | 7/1997 |
| WO | WO-9801091 A1 | 1/1998 |
| WO | WO-9855052 A1 | 12/1998 |
| WO | WO-9909914 A1 | 3/1999 |
| WO | WO-9956676 A1 | 11/1999 |
| WO | WO-9963914 A1 | 12/1999 |
| WO | WO-0024327 A2 | 5/2000 |
| WO | WO-0170141 A1 | 9/2001 |
| WO | WO-0187194 A1 | 11/2001 |
| WO | WO-0213732 A2 | 2/2002 |
| WO | WO-02058599 A2 | 8/2002 |
| WO | WO-02089701 A2 | 11/2002 |
| WO | WO-03005939 A2 | 1/2003 |
| WO | WO-2004034935 A1 | 4/2004 |
| WO | WO-2004041129 A1 | 5/2004 |
| WO | WO-2004080356 A2 | 9/2004 |
| WO | WO-2004089256 A1 | 10/2004 |
| WO | WO-2006047587 A2 | 5/2006 |
| WO | WO-2006102269 A2 | 9/2006 |
| WO | WO-2006120505 A1 | 11/2006 |
| WO | WO-2007078978 A2 | 7/2007 |
| WO | WO-2007093900 A2 | 8/2007 |
| WO | WO-2008044057 A1 | 4/2008 |
| WO | WO-2008149223 A2 | 12/2008 |
| WO | WO-2009033100 A1 | 3/2009 |
| WO | WO-2010090801 A2 | 8/2010 |
| WO | WO-2011080535 A1 | 7/2011 |
| WO | WO 2011129973 A1 | 10/2011 |
| WO | WO-2013124453 A1 | 8/2013 |
| WO | WO-2014184367 A1 | 11/2014 |
| WO | WO-2015114122 A1 | 8/2015 |

OTHER PUBLICATIONS

U.S. Appl. No. 12/279,664 U.S. Pat. No. 8,241,359, filed Apr. 22, 2009, Transforaminal Intersomatic Cage for an Intervertebral Fusion Graft and an Instrument for Implanting the Cage.
U.S. Appl. No. 13/585,063 U.S. Pat. No. 9,713,535, filed Aug. 14, 2012, Transforaminal Intersomatic Cage for an Intervertebral Fusion Graft and an Instrument for Implanting the Cage.
U.S. Appl. No. 15/465,143, filed Mar. 21, 2017, Transforaminal Intersomatic Cage for an Intervertebral Fusion Graft and an Instrument for Implanting the Cage.
U.S. Appl. No. 13/854,808 U.S. Pat. No. 9,597,198, filed Apr. 1, 2013, Transforaminal Intersomatic Cage for an Intervertebral Fusion Graft and an Instrument for Implanting the Cage.
"U.S. Appl. No. 10/276,712, Advisory Action dated Feb. 8, 2006", 3 pgs.
"U.S. Appl. No. 10/276,712, Final Office Action dated Nov. 14, 2005", 7 pgs.
"U.S. Appl. No. 10/276,712, Final Office Action dated Dec. 20, 2006", 7 pgs.
"U.S. Appl. No. 10/276,712, Final Office Action dated Dec. 23, 2004", 6 pgs.
"U.S. Appl. No. 10/276,712, Non Final Office Action dated May 27, 2005", 7 pgs.
"U.S. Appl. No. 10/276,712, Non Final Office Action dated Jun. 7, 2006", 7 pgs.
"U.S. Appl. No. 10/276,712, Non Final Office Action dated Jun. 30, 2004", 9 pgs.
"U.S. Appl. No. 10/276,712, Notice of Allowance dated Jul. 30, 2007", 4 pgs.
"U.S. Appl. No. 10/276,712, Response filed Jan. 17, 2006 to Final Office Action dated Nov. 14, 2005", 9 pgs.
"U.S. Appl. No. 10/276,712, Response filed Mar. 1, 2005 to Final Office Action dated Dec. 23, 2004", 10 pgs.
"U.S. Appl. No. 10/276,712, Response filed Jun. 19, 2007 to Final Office Action dated Dec. 20, 2006", 10 pgs.
"U.S. Appl. No. 10/276,712, Response filed Aug. 29, 2005 to Non Final Office Action dated May 27, 2005", 12 pgs.
"U.S. Appl. No. 10/276,712, Response filed Sep. 27, 2004 to Non Final Office Action dated Jun. 30, 2004", 12 pgs.
"U.S. Appl. No. 10/276,712, Response filed Oct. 6, 2006 to Non Final Office Action dated Jun. 7, 2006", 12 pgs.
"U.S. Appl. No. 10/483,563, Corrected Notice of Allowance dated Jun. 19, 2009", 4 pgs.
"U.S. Appl. No. 10/483,563, Final Office Action dated Oct. 28, 2008", 9 pgs.
"U.S. Appl. No. 10/483,563, Non Final Office Action dated Jan. 31, 2008", 8 pgs.
"U.S. Appl. No. 10/483,563, Non Final Office Action dated Feb. 21, 2007", 6 pgs.
"U.S. Appl. No. 10/483,563, Non Final Office Action dated Oct. 30, 2007", 6 pgs.
"U.S. Appl. No. 10/483,563, Response filed Apr. 28, 2009 to Final Office Action dated Oct. 28, 2008", 8 pgs.
"U.S. Appl. No. 10/483,563, Response filed Jul. 31, 2008 to Non Final Office Action dated Jan. 31, 2008", 13 pgs.
"U.S. Appl. No. 10/483,563, Response filed Aug. 21, 2007 to Non Final Office Action dated Feb. 21, 2007", 12 pgs.
"U.S. Appl. No. 10/483,563, Response filed Nov. 19, 2007 to Non Final Office Action dated Oct. 30, 2007", 4 pgs.
"U.S. Appl. No. 11/109,276, Final Office Action dated Jul. 24, 2008", 12 pgs.
"U.S. Appl. No. 11/109,276, Non Final Office Action dated Feb. 6, 2007", 12 pgs.
"U.S. Appl. No. 11/109,276, Non Final Office Action dated Feb. 13, 2009", 5 pgs.
"U.S. Appl. No. 11/109,276, Non Final Office Action dated Oct. 16, 2007", 12 pgs.
"U.S. Appl. No. 11/109,276, Notice of Allowance dated Dec. 8, 2009", 8 pgs.
"U.S. Appl. No. 11/109,276, Response filed Jan. 26, 2009 to Final Office Action dated Jul. 24, 2008", 9 pgs.
"U.S. Appl. No. 11/109,276, Response filed Apr. 16, 2008 to Non Final Office Action dated Oct. 16, 2007", 16 pgs.
"U.S. Appl. No. 11/109,276, Response filed Aug. 4, 2009 to Non Final Office Action dated Feb. 13, 2009", 8 pgs.
"U.S. Appl. No. 11/109,276, Response filed Aug. 6, 2007 to Non Final Office Action dated Feb. 6, 2007", 39 pgs.
"U.S. Appl. No. 11/378,165, Advisory Action dated Aug. 11, 2009", 3 pgs.
"U.S. Appl. No. 11/378,165, Applicant's Summary of Examiner Interview filed Jun. 18, 2010", 1 pg.
"U.S. Appl. No. 11/378,165, Examiner Interview Summary dated May 20, 2010", 3 pgs.
"U.S. Appl. No. 11/378,165, Final Office Action dated Feb. 17, 2009", 16 pgs.
"U.S. Appl. No. 11/378,165, Final Office Action dated Sep. 24, 2010", 18 pgs.

(56) References Cited

OTHER PUBLICATIONS

"U.S. Appl. No. 11/378,165, Non Final Office Action dated May 27, 2008", 15 pgs.
"U.S. Appl. No. 11/378,165, Non Final Office Action dated Oct. 26, 2009", 24 pgs.
"U.S. Appl. No. 11/378,165, Response filed Feb. 28, 2008 to Restriction Requirement dated Sep. 28, 2007", 12 pgs.
"U.S. Appl. No. 11/378,165, Response filed Mar. 24, 2011 to Final Office Action dated Sep. 24, 2010", 15 pgs.
"U.S. Appl. No. 11/378,165, Response filed Apr. 26, 2010 to Non Final Office Action dated Oct. 26, 2009", 12 pgs.
"U.S. Appl. No. 11/378,165, Response filed Aug. 4, 2009 to Final Office Action dated Feb. 17, 2009", 14 pgs.
"U.S. Appl. No. 11/378,165, Response filed Nov. 26, 2008 to Non Final Office Action dated Apr. 27, 2008", 5 pgs.
"U.S. Appl. No. 11/378,165, Restriction Requirement dated Sep. 28, 2007", 9 pgs.
"U.S. Appl. No. 11/767,386, Final Office Action dated Mar. 24, 2011", 11 pgs.
"U.S. Appl. No. 11/767,386, Non Final Office Action dated Jul. 21, 2010", 10 pgs.
"U.S. Appl. No. 11/767,386, Response filed Jan. 21, 2011 to Non Final Office Action dated Jul. 21, 2010", 21 pgs.
"U.S. Appl. No. 11/767,386, Response filed Apr. 26, 2010 to Restriction Requirement dated Dec. 24, 2009", 9 pgs.
"U.S. Appl. No. 11/767,386, Response filed Sep. 26, 2011 to Final Office Action dated Mar. 24, 2011", 18 pgs.
"U.S. Appl. No. 11/767,386, Restriction Requirement dated Dec. 24, 2009", 5 pgs.
"U.S. Appl. No. 12/134,884, Non Final Office Action dated Jan. 31, 2012", 7 pgs.
"U.S. Appl. No. 12/360,050, Non Final Office Action dated Sep. 6, 2011", 11 pgs.
"U.S. Appl. No. 12/360,050, Non Final Office Action dated Dec. 17, 2010", 14 pgs.
"U.S. Appl. No. 12/360,050, Notice of Allowance dated Mar. 26, 2012", 5 pgs.
"U.S. Appl. No. 12/360,050, Response filed Mar. 6, 2012 to Non Final Office Action dated Sep. 6, 2011", 14 pgs.
"U.S. Appl. No. 12/360,050, Response filed Jun. 16, 2011 to Non Final Office Action dated Dec. 17, 2010", 34 pgs.
"U.S. Appl. No. 12/430,768, Corrected Notice of Allowance dated Jan. 19, 2012", 2 pgs.
"U.S. Appl. No. 13/520,041, 312 Amendment filed Jun. 7, 2016", 11 pgs.
"U.S. Appl. No. 13/732,244, Final Office Action dated Jun. 8, 2016", 7 pgs.
"U.S. Appl. No. 13/854,808, Notice of Allowance dated Jul. 21, 2016", 10 pgs.
"U.S. Appl. No. 13/854,808, Notice of Allowance dated Nov. 2, 2016", 10 pgs.
"U.S. Appl. No. 13/854,808, Preliminary Amendment filed Apr. 1, 2013", 9 pgs.
"U.S. Appl. No. 13/854,808, Response filed Jun. 22, 2016 to Final Office Action dated Mar. 22, 2016", 13 pgs.
"U.S. Appl. No. 13/854,808, Supplemental Amendment filed Oct. 20, 2016", 11 pgs.
"U.S. Appl. No. 14/149,357, Advisory Action dated Jun. 1, 2016", 3 pgs.
"U.S. Appl. No. 14/149,357, Response filed May 10, 2016 to Final Office Action dated Feb. 10, 2016", 20 pgs.
"U.S. Appl. No. 14/149,357, Response filed Jun. 8, 2016 to Advisory Action dated Jun. 1, 2016", 23 pgs.
"U.S. Appl. No. 14/149,357, Supplemental Amendment filed Jul. 8, 2016", 22 pgs.
"U.S. Appl. No. 14/721,818, Advisory Action dated Jun. 1, 2016", 3 pgs.
"U.S. Appl. No. 14/721,818, Response filed May 2, 2016 to Final Office Action dated Feb. 1, 2016", 13 pgs.
"U.S. Appl. No. 14/726,558, Non Final Office Action dated Jun. 22, 2016", 13 pgs.
"U.S. Appl. No. 15/465,143, Non Final Office Action dated Dec. 8, 2017", 13 pgs.
"U.S. Appl. No. 15/465,143, Notice of Allowance dated Jul. 19, 2018", 9 pgs.
"U.S. Appl. No. 15/465,143, Preliminary Amendment filed Mar. 21, 2017", 10 pgs.
"U.S. Appl. No. 15/465,143, Response filed Mar. 8, 2018 to Non Final Office Action dated Dec. 8, 2017", 15 pgs.
"U.S. Appl. No. 15/465,143, Response filed Nov. 29, 2017 to Restriction Requirement dated Sep. 29, 2017", 6 pgs.
"U.S. Appl. No. 15/465,143, Restriction Requirement dated Sep. 29, 2017", 8 pgs.
"European Application Serial No. 07733892.9, Communication Pursuant to Article 94(3) EPC dated Dec. 17, 2013", 5 pgs.
"European Application Serial No. 07733892.9, Response filed Feb. 17, 2014 to Communication Pursuant to Article 94(3) EPC dated Dec. 17, 2013", 26 pgs.
"European Application Serial No. 07733892.9, Response filed Nov. 26, 2008 to Communication pursuant to Rules 161(1) and 162 EPC dated Oct. 27, 2008", 16 pgs.
"European Application Serial No. 08762820.2, Amendment filed Jan. 6, 2010", 23 pgs.
"European Application Serial No. 09812464.7, Communication Pursuant to Article 94(3) EPC dated Mar. 3, 2016", 6 pgs.
"European Application Serial No. 09812464.7, Response filed Mar. 25, 2013 to Communication Pursuant to Rules 161(1) and 162 EPC dated Sep. 25, 2012", 30 pgs.
"European Application Serial No. 11165170.9, Extended European Search Report dated Jul. 21, 2011", 7 pgs.
"European Application Serial No. 11165170.9, Response filed Mar. 6, 2012 to Extended European Search Report dated Jul. 21, 2011", 17 pgs.
"France Application Serial No. 0006351, Search Report dated Jan. 29, 2001", 1 pg.
"France Application Serial No. 0109381, Search Report dated Apr. 5, 2002", 2 pgs.
"France Application Serial No. 0413728, Preliminary Search Report dated Aug. 11, 2005", 2 pgs.
"France Application Serial No. 2897259, Search Report dated Oct. 11, 2006", 2 pgs.
"France Application Serial No. 2916956, Preliminary Search Report dated Jan. 30, 2008", 3 pgs.
"French Application Serial No. 2808995, Preliminary Search Report dated Jan. 29, 2001", 1 pg.
"French Application Serial No. 2827156, Preliminary Search Report dated Apr. 5, 2002", 2 pgs.
"International Application Serial No. PCT/FR2001/001545, International Preliminary Examination Report dated Aug. 30, 2002", 16 pgs.
"International Application Serial No. PCT/FR2001/001545, International Search Report dated Sep. 5, 2001", 3 pgs.
"International Application Serial No. PCT/IB2002/003390, International Preliminary Examination Report dated Nov. 6, 2003", 4 pgs.
"International Application Serial No. PCT/IB2002/003390, International Search Report dated Mar. 3, 2003", 2 pgs.
"International Application Serial No. PCT/IB2005/004093, International Preliminary Report on Patentability dated Feb. 22, 2007", 8 pgs.
"International Application Serial No. PCT/IB2005/004093, International Search Report dated Aug. 31, 2006", 3 pgs.
"International Application Serial No. PCT/IB2005/004093, Written Opinion dated Aug. 31, 2006", 5 pgs.
"International Application Serial No. PCT/IB2007/000367, International Preliminary Report on Patentability dated Feb. 5, 2008", 9 pgs.
"International Application Serial No, PCT/IB2007/000367, International Search Report dated Oct. 22, 2007", 5 pgs.
"International Application Serial No. PCT/IB2007/000367, Written Opinion dated Oct. 22, 2007", 9 pgs.

(56) References Cited

OTHER PUBLICATIONS

"International Application Serial No. PCT/IB2008/001484, Amendment filed May 13, 2009", 33 pgs.
"International Application Serial No. PCT/IB2008/001484, International Preliminary Report on Patentability dated Aug. 5, 2009", 6 pgs.
"International Application Serial No. PCT/IB2008/001484, International Search Report dated Feb. 16, 2009", 5 pgs.
"International Application Serial No. PCT/IB2008/001484, Written Opinion dated Feb. 16, 2009", 8 pgs.
"Lateral definition", Dictionary.com, [Online]. [Accessed Feb. 6, 2009]. Retrieved from the Internet: <URL: http://dictionary.reference.com/browse/lateral >, 4 pgs.
"LDR Medical, by its attorneys; Chapter II amendments for PCT Pub'n No. WO2006120505", App. No. PCT/IB2005/004093; Oct. 30, 2006; WIPO, 14 pgs.
"LDR Medical; Greffe et fusion", LDR Medical; France, (Sep. 19, 2004), 1 pg.
"LDR Medical; ROI Privilegier la greffe en creant la chambre de fusion", LDR Medical, (Sep. 19, 2004), 1 pg.
"Mc+ Le choix de l'ancrage", LDR Medical, (Sep. 19, 2004), 1 pg.
"Request for Continued Examination in U.S. Appl. No. 11/378,165, filed Aug. 14, 2009", LDR Medical, by its attorneys, USPTO; Alexandria, Virgina, 1 pg.
"U.S. Appl. No. 10/276,712, Response filed Mar. 14, 2006 to Advisory Action dated Feb. 8, 2006", 8 pgs.
"U.S. Appl. No. 10/483,563, Notice of Allowance dated Jun. 5, 2009", 4 pgs.
"U.S. Appl. No. 10/533,846, Final Office Action dated Oct. 15, 2008", 13 pgs.
"U.S. Appl. No. 10/533,846, Non Final Office Action dated Apr. 18, 2007", 11 pgs.
"U.S. Appl. No. 10/533,846, Non Final Office Action dated Dec. 26, 2007", 14 pgs.
"U.S. Appl. No. 10/533,846, Notice of Allowance dated Nov. 4, 2009", 4 pgs.
"U.S. Appl. No. 10/533,846, Response filed Apr. 15, 2009 to Final Office Action dated Oct. 15, 2008", 13 pgs.
"U.S. Appl. No. 10/533,846, Response filed Jun. 25, 20-08 to Non Final Office Action dated Dec. 26, 2007", 18 pgs.
"U.S. Appl. No. 10/533,846, Response filed Oct. 16, 2007 to Non Final Office Action dated Apr. 18, 2007", 16 pgs.
"U.S. Appl. No. 11/341,007, Final Office Action dated Dec. 17, 2009", 17 pgs.
"U.S. Appl. No. 11/341,007, Non Final Office Action dated Apr. 13, 2009", 13 pgs.
"U.S. Appl. No. 11/341,007, Notice of Allowance dated Jul. 26, 2010", 6 pgs.
"U.S. Appl. No. 11/341,007, Response filed Jun. 17, 2010 to Final Office Action dated Dec. 17, 2009", 12 pgs.
"U.S. Appl. No. 11/341,007, Response filed Oct. 13, 2009 to Non Final Office Action dated Apr. 13, 2009", 15 pgs.
"U.S. Appl. No. 11/378,165, Applicant's Summary of Examiner Interview filed Feb. 26, 2013", 3 pgs.
"U.S. Appl. No. 11/378,165, Non Final Office Action dated Jun. 4, 2012", 27 pgs.
"U.S. Appl. No. 11/378,165, Notice of Allowance dated Nov. 26, 2012", 10 pgs.
"U.S. Appl. No. 11/378,165, Response filed Nov. 5, 2012 to Non Final Office Action dated Jun. 4, 2012", 14 pgs.
"U.S. Appl. No. 11/767,386, Non Final Office Action dated Apr. 24, 2013", 10 pgs.
"U.S. Appl. No. 11/767,386, Notice of Allowance dated Aug. 30, 2013", 6 pgs.
"U.S. Appl. No. 11/767,386, Response filed Jul. 24, 2013 to Non Final Office Action dated Apr. 24, 2013", 14 pgs.
"U.S. Appl. No. 11/767,386, Response to Statement of Reasons for Allowance dated Dec. 2, 2013", 2 pgs.
"U.S. Appl. No. 12/134,884, Notice of Allowance dated Nov. 1, 2012", 7 pgs.

"U.S. Appl. No. 12/134,884, Response filed Jul. 31, 2012 to Non Final Office Action dated Jan. 31, 2012", 20 pgs.
"U.S. Appl. No. 12/279,664, Non Final Office Action dated Sep. 14, 2011", 13 pgs.
"U.S. Appl. No. 12/279,664, Notice of Allowance dated Apr. 11, 2012", 11 pgs.
"U.S. Appl. No. 12/279,664, Notice of Allowance dated May 29, 2012", 4 pgs.
"U.S. Appl. No. 12/279,664, Response filed Mar. 14, 2012 to Non Final Office Action dated Sep. 14, 2011", 21 pgs.
"U.S. Appl. No. 12/360,050, Notice of Allowance dated May 18, 2012", 4 pgs.
"U.S. Appl. No. 12/360,050, Notice of Allowance dated Jul. 6, 2012", 5 pgs.
"U.S. Appl. No. 12/360,050, Notice of Allowance dated Aug. 2, 2012", 2 pgs.
"U.S. Appl. No. 12/424,364, Applicant's Summary of Examiner Interview filed May 22, 2012", 3 pgs.
"U.S. Appl. No. 12/424,364, Non Final Office Action dated Jan. 26, 2012", 10 pgs.
"U.S. Appl. No. 12/424,364, Non Final Office Action dated May 18, 2011", 10 pgs.
"U.S. Appl. No. 12/424,364, Non Final Office Action dated May 23, 2012", 6 pgs.
"U.S. Appl. No. 12/424,364, Notice of Allowance dated Jul. 24, 2012", 5 pgs.
"U.S. Appl. No. 12/424,364, Notice of Allowance dated Aug. 2, 2012", 2 pgs.
"U.S. Appl. No. 12/424,364, Response filed Feb. 27, 2012 to Non Final Office Action dated Jan. 26, 2012", 6 pgs.
"U.S. Appl. No. 12/424,364, Response filed Jul. 6, 2012 to Non Final Office Action dated May 23, 2012", 4 pgs.
"U.S. Appl. No. 12/424,364, Response filed Nov. 18, 2011 to Non Final Office Action dated May 18, 2011", 13 pgs.
"U.S. Appl. No. 12/430,768, Non Final Office Action dated Jun. 14, 2011", 7 pgs.
"U.S. Appl. No. 12/430,768, Notice of Allowance dated Jan. 11, 2012", 5 pgs.
"U.S. Appl. No. 12/430,768, Response filed Dec. 14, 2011 to Non Final Office Action dated Jun. 14, 2011", 7 pgs.
"U.S. Appl. No. 12/884,664, Examiner Interview Summary dated Dec. 18, 2012", 2 pgs.
"U.S. Appl. No. 12/884,664, Non Final Office Action dated Jan. 15, 2013", 7 pgs.
"U.S. Appl. No. 12/884,664, Notice of Allowance dated Aug. 6, 2013", 9 pgs.
"U.S. Appl. No. 12/884,664, Response filed Apr. 10, 2013 to Non Final Office Action dated Jan. 15, 2013", 16 pgs.
"U.S. Appl. No. 12/884,664, Response filed Oct. 16, 2012 to Restriction Requirement dated Sep. 26, 2012", 15 pgs.
"U.S. Appl. No. 12/884,664, Restriction Requirement dated Sep. 26, 2012", 6 pgs.
"U.S. Appl. No. 12/955,898, Final Office Action dated Jan. 10, 2013", 17 pgs.
"U.S. Appl. No. 12/955,898, Non Final Office Action dated Mar. 3, 2014", 11 pgs.
"U.S. Appl. No. 12/955,898, Non Final Office Action dated Jun. 1, 2012", 27 pgs.
"U.S. Appl. No. 12/955,898, Notice of Allowance dated Jan. 29, 2015", 7 pgs.
"U.S. Appl. No. 12/955,898, Notice of Allowance dated Aug. 8, 2014", 7 pgs.
"U.S. Appl. No. 12/955,898, Response filed Apr. 19, 2012 to Restriction Requirement dated Mar. 19, 2012", 11 pgs.
"U.S. Appl. No. 12/955,898, Response filed Jul. 10, 2013 to Final Office Action dated Jan. 10, 2013", 12 pgs.
"U.S. Appl. No. 12/955,898, Response filed Aug. 4, 2014 to Non Final Office Action dated Mar. 3, 2014", 11 pgs.
"U.S. Appl. No. 12/955,898, Response filed Dec. 3, 2012 to Non Final Office Action dated Jun. 1, 2012", 20 pgs.
"U.S. Appl. No. 12/955,898, Restriction Requirement dated Mar. 19, 2012", 9 pgs.

(56) References Cited

OTHER PUBLICATIONS

"U.S. Appl. No. 13/158,761, Examiner Interview Summary dated Aug. 1, 2013", 3 pgs.
"U.S. Appl. No. 13/158,761, Examiner Interview Summary dated Oct. 31, 2012", 3 pgs.
"U.S. Appl. No. 13/158,761, Final Office Action dated Aug. 14, 2013", 11 pgs.
"U.S. Appl. No. 13/158,761, Final Office Action dated Oct. 22, 2014", 12 pgs.
"U.S. Appl. No. 13/158,761, Non Final Office Action dated Feb. 28, 2013", 10 pgs.
"U.S. Appl. No. 13/158,761, Notice of Allowance dated May 12, 2015", 5 pgs.
"U.S. Appl. No. 13/158,761, Notice of Allowance dated Sep. 2, 2015", 5 pgs.
"U.S. Appl. No. 13/158,761, Response filed Apr. 22, 2015 to Final Office Action dated Oct. 22, 2014", 10 pgs.
"U.S. Appl. No. 13/158,761, Response filed Jul. 29, 2013 to Non Final Office Action dated Feb. 28, 2013", 12 pgs.
"U.S. Appl. No. 13/158,761, Response filed Nov. 14, 2013 to Final Office Action dated Aug. 14, 2013", 12 pgs.
"U.S. Appl. No. 13/158,761, Response filed Nov. 19, 2012 to Restriction Requirement dated Oct. 17, 2012", 8 pgs.
"U.S. Appl. No. 13/158,761, Restriction Requirement dated Oct. 17, 2012", 6 pgs.
"U.S. Appl. No. 13/158,761, Supplemental Notice of Allowability dated Sep. 25, 2015", 2 pgs.
"U.S. Appl. No. 13/438,352, Non Final Office Action dated Aug. 14, 2014", 8 pgs.
"U.S. Appl. No. 13/438,352, Notice of Allowance dated Mar. 2, 2015", 7 pgs.
"U.S. Appl. No. 13/438,352, Response filed Jan. 14, 2015 to Non Final Office Action dated Aug. 14, 2014", 10 pgs.
"U.S. Appl. No. 13/520,041, Final Office Action dated Oct. 6, 2014", 10 pgs.
"U.S. Appl. No. 13/520,041, Non Final Office Action dated Mar. 20, 2014", 9 pgs.
"U.S. Appl. No. 13/520,041, Non Final Office Action dated Apr. 10, 2015", 7 pgs.
"U.S. Appl. No. 13/520,041, Notice of Allowance dated Mar. 8, 2016", 5 pgs.
"U.S. Appl. No. 13/520,041, Notice of Allowance dated Nov. 18, 2015", 5 pgs.
"U.S. Appl. No. 13/520,041, Response filed Mar. 6, 2015 to Final Office Action dated Oct. 6, 2014", 12 pgs.
"U.S. Appl. No. 13/520,041, Response filed Aug. 10, 2015 to Non Final Office Action dated Apr. 10, 2015", 11 pgs.
"U.S. Appl. No. 13/520,041, Response filed Sep. 19, 2014 to Non Final Office Action dated Mar. 20, 2014", 5 pgs.
"U.S. Appl. No. 13/538,078, Non Final Office Action dated May 12, 2014", 12 pgs.
"U.S. Appl. No. 13/538,078, Notice of Allowance dated Oct. 20, 2014", 5 pgs.
"U.S. Appl. No. 13/538,078, Response filed Oct. 14, 2014 to Non Final Office Action dated May 12, 2014", 10 pgs.
"U.S. Appl. No. 13/585,063, Applicant's Summary of Examiner Interview filed Jun. 20, 2017", 3 pgs.
"U.S. Appl. No. 13/585,063, Examiner Interview Summary dated Feb. 6, 2017", 3 pgs.
"U.S. Appl. No. 13/585,063, Final Office Action dated Nov. 4, 2015", 17 pgs.
"U.S. Appl. No. 13/585,063, Final Office Action dated Nov. 30, 2016", 11 pgs.
"U.S. Appl. No. 13/585,063, Non Final Office Action dated Feb. 11, 2015", 13 pgs.
"U.S. Appl. No. 13/585,063, Non Final Office Action dated Jun. 17, 2016", 16 pgs.
"U.S. Appl. No. 13/585,063, Notice of Allowance dated Mar. 20, 2017", 9 pgs.
"U.S. Appl. No. 13/585,063, Preliminary Amendment filed Aug. 14, 2012", 13 pgs.
"U.S. Appl. No. 13/585,063, Response filed Jan. 6, 2015 to Restriction Requirement dated Nov. 6, 2014", 9 pgs.
"U.S. Appl. No. 13/585,063, Response filed Feb. 4, 2016 to Final Office Action dated Nov. 4, 2015", 9 pgs.
"U.S. Appl. No. 13/585,063, Response filed Feb. 28, 2017 to Final Office Action dated Nov. 30, 2016", 12 pgs.
"U.S. Appl. No. 13/585,063, Response filed Aug. 11, 2015 to Non Final Office Action dated Feb. 11, 2015", 14 pgs.
"U.S. Appl. No. 13/585,063, Response filed Sep. 19, 2016 to Non Final Office Action dated Jun. 17, 2016", 18 pgs.
"U.S. Appl. No. 13/585,063, Restriction Requirement dated Nov. 6, 2014", 8 pgs.
"U.S. Appl. No. 13/585,063, Supplemental Amendment filed May 4, 2016", 11 pgs.
"U.S. Appl. No. 13/603,043, Final Office Action dated Jul. 24, 2014", 11 pgs.
"U.S. Appl. No. 13/603,043, Non Final Office Action dated Apr. 9, 2013", 13 pgs.
"U.S. Appl. No. 13/603,043, Non Final Office Action dated Nov. 21, 2013", 11 pgs.
"U.S. Appl. No. 13/603,043, Notice of Allowance dated Feb. 10, 2015", 5 pgs.
"U.S. Appl. No. 13/603,043, Response filed May 21, 2014 to Non Final Office Action dated Nov. 21, 2013", 13 pgs.
"U.S. Appl. No. 13/603,043, Response filed Oct. 9, 2013 to Non Final Office Action dated Apr. 9, 2013", 37 pgs.
"U.S. Appl. No. 13/603,043, Response filed Dec. 24, 2014 to Final Office Action dated Jul. 24, 2014", 11 pgs.
"U.S. Appl. No. 13/616,448, Non Final Office Action dated Aug. 22, 2013", 6 pgs.
"U.S. Appl. No. 13/616,448, Notice of Allowance dated Feb. 7, 2014", 5 pgs.
"U.S. Appl. No. 13/616,448, Notice of Allowance dated Apr. 21, 2014", 2 pgs.
"U.S. Appl. No. 13/616,448, Response filed Dec. 23, 2013 to Non Final Office Action dated Aug. 22, 2013", 9 pgs.
"U.S. Appl. No. 13/732,244, Final Office Action dated Feb. 20, 2015", 9 pgs.
"U.S. Appl. No. 13/732,244, Non Final Office Action dated Sep. 19, 2014", 4 pgs.
"U.S. Appl. No. 13/732,244, Non Final Office Action dated Oct. 20, 2015", 6 pgs.
"U.S. Appl. No. 13/732,244, Response filed Jan. 20, 2015 to Non Final Office Action dated Sep. 19, 2014", 12 pgs.
"U.S. Appl. No. 13/732,244, Response filed Jan. 20, 2016 to Non Final Office Action dated Oct. 20, 2015", 16 pgs.
"U.S. Appl. No. 13/732,244, Response filed Jul. 30, 2014 to Restriction Requirement dated Apr. 30, 2014", 4 pgs.
"U.S. Appl. No. 13/732,244, Response filed Aug. 20, 2015 to Final Office Action dated Feb. 20, 2015", 13 pgs.
"U.S. Appl. No. 13/732,244, Restriction Requirement dated Apr. 30, 2014", 5 pgs.
"U.S. Appl. No. 13/774,547, Notice of Allowance dated Feb. 2, 2015", 5 pgs.
"U.S. Appl. No. 13/774,547, Notice of Allowance dated Jul. 3, 2014", 12 pgs.
"U.S. Appl. No. 13/774,547, Notice of Allowance dated Oct. 16, 2014", 8 pgs.
"U.S. Appl. No. 13/854,808, Examiner Interview Summary dated Mar. 30, 2016", 3 pgs.
"U.S. Appl. No. 13/854,808, Final Office Action dated Jan. 23, 2015", 16 pgs.
"U.S. Appl. No. 13/854,808, Final Office Action dated Mar. 22, 2016", 10 pgs.
"U.S. Appl. No. 13/854,808, Non Final Office Action dated Jul. 7, 2014", 12 pgs.
"U.S. Appl. No. 13/854,808, Non Final Office Action dated Nov. 27, 2015", 9 pgs.
"U.S. Appl. No. 13/854,808, Response filed Jan. 7, 2015 to Non Final Office dated Jul. 7, 2014", 12 pgs.

(56) References Cited

OTHER PUBLICATIONS

"U.S. Appl. No. 13/854,808, Response filed Feb. 29, 2016 to Non Final Office Action dated Nov. 27, 2015", 13 pgs.
"U.S. Appl. No. 13/854,808, Response filed Jun. 18, 2014 to Restriction Requirement dated Apr. 18, 2014", 9 pgs.
"U.S. Appl. No. 13/854,808, Response filed Jul. 23, 2015 to Final Office Action dated Jan. 23, 2015", 12 pgs.
"U.S. Appl. No. 13/854,808, Restriction Requirement dated Apr. 18, 2014", 9 pgs.
"U.S. Appl. No. 14/064,434, Non Final Office Action dated May 5, 2014", 7 pgs.
"U.S. Appl. No. 14/064,434, Notice of Allowance dated Sep. 9, 2014", 5 pgs.
"U.S. Appl. No. 14/064,434, Response filed Apr. 14, 2014 to Restriction Requirement dated Jan. 13, 2014", 21 pgs.
"U.S. Appl. No. 14/064,434, Response filed Aug. 27, 2014 to Non Final Office Action dated May 5, 2014", 12 pgs.
"U.S. Appl. No. 14/064,434, Restriction Requirement dated Jan. 13, 2014", 6 pgs.
"U.S. Appl. No. 14/149,357, Final Office Action dated Feb. 10, 2016", 13 pgs.
"U.S. Appl. No. 14/149,357, Non Final Office Action dated Sep. 11, 2015", 10 pgs.
"U.S. Appl. No. 14/149,357, Response filed Aug. 31, 2015 to Restriction Requirement dated Jun. 30, 2015", 10 pgs.
"U.S. Appl. No. 14/149,357, Response filed Dec. 11, 2015 to Non Final Office Action dated Sep. 11, 2015", 16 pgs.
"U.S. Appl. No. 14/149,357, Restriction Requirement dated Jun. 30, 2015", 6 pgs.
"U.S. Appl. No. 14/306,785, Final Office Action dated Jun. 22, 2015", 9 pgs.
"U.S. Appl. No. 14/306,785, Non Final Office Action dated Oct. 22, 2014", 6 pgs.
"U.S. Appl. No. 14/306,785, Notice of Allowance dated Oct. 13, 2015", 6 pgs.
"U.S. Appl. No. 14/306,785, Response filed Apr. 22, 2015 to Non Final Office Action dated Oct. 22, 2014", 9 pgs.
"U.S. Appl. No. 14/306,785, Response filed Sep. 22, 2015 to Final Office Action dated Jun. 22, 2015", 11 pgs.
"U.S. Appl. No. 14/594,770, Non Final Office Action dated Jan. 27, 2016", 8 pgs.
"U.S. Appl. No. 14/594,770, Response filed Apr. 27, 2006 to Non Final Office Action dated Jan. 27, 2016", 14 pgs.
"U.S. Appl. No. 14/594,770, Response filed Nov. 2, 2015 to Restriction Requirement dated Jul. 1, 2015", 11 pgs.
"U.S. Appl. No. 14/594,770, Restriction Requirement dated Jul. 1, 2015", 6 pgs.
"U.S. Appl. No. 14/659,587, Non Final Office Action dated Jan. 28, 2016", 10 pgs.
"U.S. Appl. No. 14/659,587, Non Final Office Action dated Apr. 16, 2015", 12 pgs.
"U.S. Appl. No. 14/659,587, Notice of Allowance dated Oct. 9, 2015", 6 pgs.
"U.S. Appl. No. 14/659,587, Response filed Apr. 28, 2016 to Non Final Office Action dated Jan. 28, 2016", 14 pgs.
"U.S. Appl. No. 14/659,587, Response filed Sep. 16, 2015 to Non Final Office Action dated Apr. 16, 2015", 13 pgs.
"U.S. Appl. No. 14/721,818, Final Office Action dated Feb. 1, 2016", 19 pgs.
"U.S. Appl. No. 14/721,818, Non Final Office Action dated Sep. 24, 2015", 21 pgs.
"U.S. Appl. No. 14/721,818, Response filed Dec. 28, 2015 to Non Final Office Action dated Sep. 24, 2015", 15 pgs.
"U.S. Appl. No. 14/726,557, Non Final Office Action dated Dec. 30, 2015", 12 pgs.
"Demand for International App. No. PCT/IB2009/008048", PCT Pub'n No. WO2011080535; Apr. 19, 2011; WIPO Geneva, Switzerland.
"European Application Serial No. 02784881.1, Intention to Grant dated Aug. 26, 2010", 24 pgs.

"European Application Serial No. 02784881.1, Office Action dated Mar. 13, 2009", 2 pgs.
"European Application Serial No. 02784881.1, Office Action dated Aug. 4, 2009", 3 pgs.
"European Application Serial No. 02784881.1, Response filed Jul. 22, 2009 to Office Action dated Mar. 13, 2009", 21 pgs.
"European Application Serial No. 02784881.1, Response filed Oct. 14, 2009 to Office Action dated Aug. 4, 2009", 20 pgs.
"European Application Serial No. 05857774.3, Communication Pursuant to Article 94(3) EPC dated Apr. 11, 2011", 4 pgs.
"European Application Serial No. 05857774.3, Communication Pursuant to Article 94(3) EPC dated May 6, 2009", 3 pgs.
"European Application Serial No. 05857774.3, Response filed Oct. 11, 2011 to Communication Pursuant to Article 94(3) EPC dated Apr. 11, 2011", 20 pgs.
"European Application Serial No. 05857774.3, Response filed Nov. 13, 2009 to Communication Pursuant to Article 94(3) EPC dated May 6, 2009", 22 pgs.
"European Application Serial No. 08762820.2, Communication Pursuant to Article 94(3) EPC dated Jan. 17, 2012", 4 pgs.
"European Application Serial No. 08762820.2, Response filed Jul. 27, 2012 to Communication Pursuant to Article 94(3) EPC dated Jan. 17, 2012", 23 pgs.
"European Application Serial No. 09009533.2, Extended European Search Report dated Oct. 6, 2009", 4 pgs.
"European Application Serial No. 09009533.2, Response filed Apr. 26, 2010 to Extended European Search Report dated Oct. 6, 2009", 10 pgs.
"European Application Serial No. 09812464.7, Amendment filed May 23, 2013", No Document Available.
"European Application Serial No. 10185004.8, Extended European Search Report dated Apr. 6, 2011", 6 pgs.
"European Application Serial No. 11157596.5, Extended European Search Report dated Jun. 8, 2011", 5 pgs.
"European Application Serial No. 11165170.9, Communication Pursuant to Article 94(3) EPC dated May 15, 2012", 5 pgs.
"European Application Serial No. 13170071.8, Extended European Search Report dated Oct. 1, 2013", 6 pgs.
"France Application Serial No. 0213833, Preliminary Search Report dated Jul. 10, 2003", 2 pgs.
"France Application Serial No. 0509740, Preliminary Search Report dated Jun. 27, 2006", 2 pgs.
"France Application Serial No. 0601315, Search Report dated Oct. 11, 2006", 2 pgs.
"France Application Serial No. 0704155, Preliminary Search Report dated Jan. 30, 2008", 3 pgs.
"France Application Serial No. 1251733, Search Report dated Dec. 5, 2012", 2 pgs.
"France Application Serial No. 1354421, Search Report dated Feb. 12, 2014", 5 pgs.
"France Application Serial No. 1450749, Search Report dated Sep. 11, 2014", 2 pgs.
"International Application Serial No. PCT/EP2013/053622, International Preliminary Report on Patentability dated Jul. 11, 2014", 4 pgs.
"International Application Serial No. PCT/EP2013/053622, International Search Report dated May 29, 2013", 3 pgs.
"International Application Serial No. PCT/EP2013/053622, Response filed Dec. 18, 2013 to International Search Report dated May 29, 2013", No Document Found/Available.
"International Application Serial No. PCT/EP2013/053622, Written Opinion dated May 29, 2013", 3 pgs.
"International Application Serial No. PCT/EP2014/060135, International Search Report dated Aug. 26, 2014", 7 pgs.
"International Application Serial No. PCT/EP2014/060135, Written Opinion dated Aug. 26, 2014", 14 pgs.
"International Application Serial No. PCT/EP2015/052019, International Search Report dated May 13, 2015", 4 pgs.
"International Application Serial No. PCT/EP2015/052019, Written Opinion dated May 13, 2015", 9 pgs.
"International Application Serial No. PCT/IB2003/004872, International Preliminary Examination Report dated Mar. 1, 2005", 6 pgs.

(56) References Cited

OTHER PUBLICATIONS

"International Application Serial No. PCT/IB2003/004872, International Search Report dated Mar. 3, 2004", 3 pgs.

"International Application Serial No. PCT/IB2006/002632, International Preliminary Report on Patentability dated Aug. 14, 2007", 5 pgs.

"International Application Serial No. PCT/IB2006/002632, International Search Report dated Feb. 23, 2007", 3 pgs.

"International Application Serial No. PCT/IB2006/002632, Written Opinion dated Feb. 23, 2007", 5 pgs.

"International Application Serial No. PCT/IB2009/008048, Amendment filed Apr. 2, 2012", 24 pgs.

"International Application Serial No. PCT/IB2009/008048, International Preliminary Report on Patentability dated Apr. 18, 2012", 20 pgs.

"International Application Serial No. PCT/IB2009/008048, International Search Report dated Feb. 2, 2011", 6 pgs.

"International Application Serial No. PCT/IB2009/008048, Written Opinion dated Feb. 2, 2011", 15 pgs.

"International Application Serial No. PCT/US2010/049287, International Preliminary Report on Patentability dated Mar. 29, 2012", 7 pgs.

"International Application Serial No. PCT/US2010/049287, International Search Report dated Jan. 11, 2011", 5 pgs.

"International Application Serial No. PCT/US2010/049287, Written Opinion dated Jan. 11, 2011", 5 pgs.

"Intervertebral Disc Prosthesis", Pub. 20090204219 U.S. Appl. No. 12/424,364, filed Apr. 15, 2009.

"Interview Summary for International App. No. PCT/IB2009/008048", PCT Pub'n No. WO2011080535; dated Feb. 14, 2012; WIPO; Geneva, Switzerland.

"Japanese Application Serial No. 20080554874, Office Action dated Nov. 4, 2011".

"Japanese Application Serial No. 20080554874, Response filed May 15, 2012 to Office Action dated Nov. 4, 2011".

"Reply to Office Action in U.S. Appl. No. 13/774,547; dated Feb. 2, 2015", USPTO; Alexandria, Virgina, 6 pgs.

"Vertebral implant and insert for vertebral implant", U.S. Appl. No. 15/144,638, filed May 2, 2016.

Brett, Darrell C, "Intervertebral Fusion Cage with Retractable-Extrudable Pins", U.S. Appl. No. 611243,297, filed Sep. 17, 2009.

Brett, Darrell C, "Intervertebral Fusion Cage with Retractable-Extrudable Pins", U.S. Appl. No. 611260,364, filed Nov. 11, 2009.

\* cited by examiner

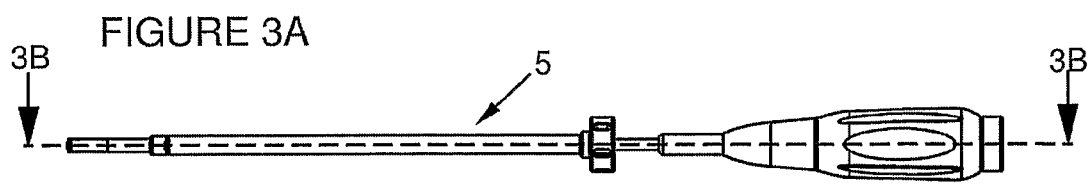
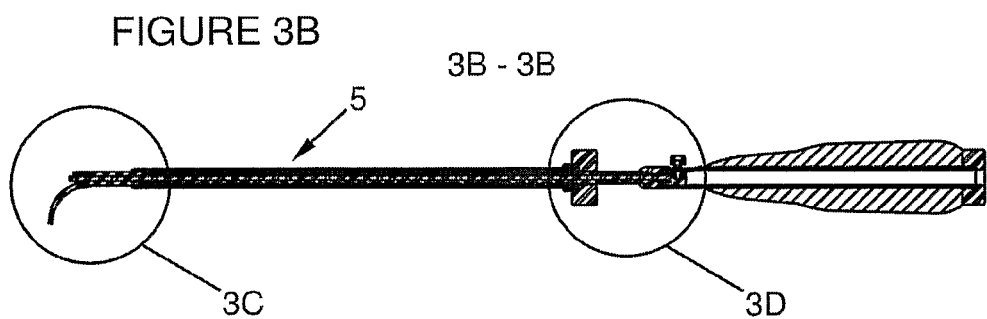
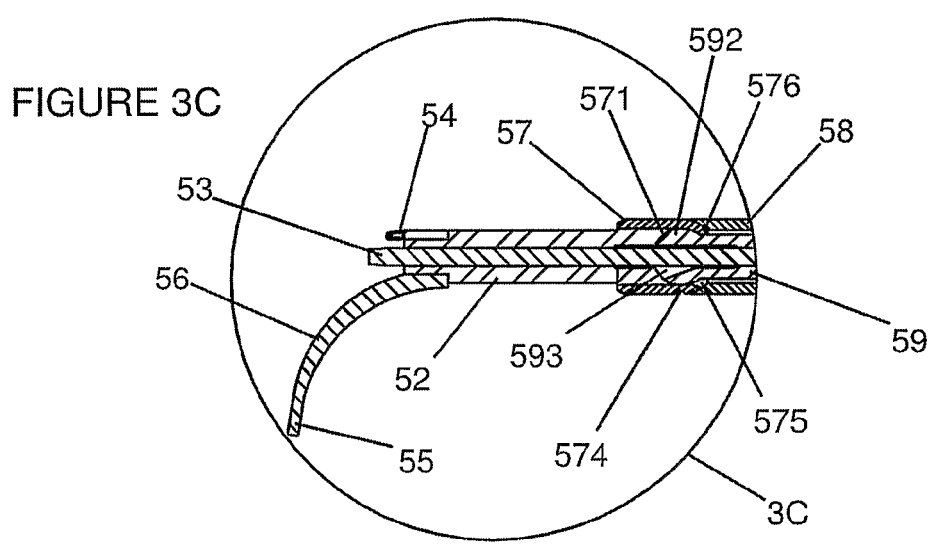

4D - 4D

TRANSFORAMINAL INTERSOMATIC CAGE FOR AN INTERVERTEBRAL FUSION GRAFT AND AN INSTRUMENT FOR IMPLANTING THE CAGE

CROSS REFERENCE TO RELATED APPLICATIONS

This application is a continuation of U.S. application Serial No. Ser. No. 13/585,063 issuing as U.S. Pat. No. 9,713,535 on Jul. 25, 2017, which is a continuation of U.S. application Ser. No. 12/279,664 issuing as U.S. Pat. No. 8,241,359 on Aug. 14, 2012, which is a national stage entry of International Application PCT/IB2007/000367 filed Feb. 15, 2007, and having a 35 U.S.C. § 371(c) date of Apr. 22, 2009, which claims the priority under 35 U.S.C. § 119 of French Patent Application No. 0601315 filed Feb. 15, 2006. Applications PCT/IB2007/000367 and FR0601315 are incorporated herein by reference for all purposes.

BACKGROUND

This present invention concerns the area of intervertebral arthrodeses (fusion of two vertebrae) and in particular of intersomatic cages implanted between two adjacent vertebrae to allow the insertion and the growth of grafts of osseous tissue (or of substitute) in the disc space. In fact, after the insertion of the cage or implant, the intervertebral space is filled with autologous spongy bone or suitable bone substitutes. The invention also concerns an instrument for implanting the cage between the vertebrae, in particular through the transforaminal approach. The intersomatic cages are designed to be positioned between two vertebrae, in order to restore and/or maintain the disc space by replacing the intervertebral disc, and the grafts of osseous tissue or of substitute are designed to allow fusion between the two adjacent vertebrae between which they are inserted.

Various types of intersomatic cage are known from prior art. Some intersomatic cages known from prior art are machined from bone, most often cortical bone, so as to fuse with the graft inserted into the disc space. These cages composed of bone have the disadvantage to being capable of causing illness in the event of imperfect sterilisation.

Different intersomatic cages in solid materials of various types are also known from prior art. These cages include openings on their lower surface, their upper surface and on at least one of their lateral surfaces. One of these cages, in particular known from patent application WO0187194 (A1) submitted by the present applicant, has the shape of an open ring and can be used in combination with another cage of the same type by placing the open lateral surfaces of the two cages opposite to each other. Whatever the type of cage in question, spongy bone is compacted inside the cage, in order to finally achieve an osseous fusion (or arthrodesis) of the two vertebrae separated by a suitable disc space. Other cages known from previous designs are of parallelepiped shape, with the top and the bottom of the cage being completely open, and the top and bottom openings being designed to be positioned facing two vertebrae which have to be kept apart from each other. Openings created in the lateral faces of the parallelepipeds allow the graft to grow toward the exterior of the cage and possibly to reach a graft implanted in another cage also inserted into the disc space. These intersomatic cages have the disadvantage, firstly, of requiring a relatively large incision in the annulus (the outer part of the intervertebral disc), secondly, of requiring a relatively long time before achieving an arthrodesis, because of the confinement of the graft within a chamber at the centre of the cage and, thirdly, of having dimensions that are too large to be implanted through the transforaminal approach without partial or total ablation of the articular processes located posterior to the foramen through which the transforaminal approach runs.

Also known from previous designs in prior art, in particular from American patent application US 2005/0038511 (A1), are intersomatic cages of various shapes and dimensions, machined from bone, and in particular an intersomatic cage of banana (or simple bracket) shape defining a longitudinal axis of the cage and having a lower surface and an upper surface, both straight, equipped with serrations and more or less parallel to the longitudinal axis of the cage, a concave lateral wall, a convex lateral wall, and two straight end walls that are more or less perpendicular to the top and bottom surfaces. One of the end walls of the cage includes a hole oriented toward the centre of the cage and intended to receive a rod of an instrument for insertion of the cage between the vertebrae. This intersomatic cage has the disadvantage of being in osseous tissue and therefore, as mentioned previously, of being capable of causing illness in the event of imperfect sterilisation. This cage may also have the disadvantage of eventually not being sufficiently solid to reliably take the stresses which will be applied to it when implanted in the disc space. Furthermore, this cage has the disadvantage of having a hole oriented toward the centre of the cage and in particular toward the centre of the concave surface, the result of which is to make the cage even more fragile. Moreover, the axis defined by this hole forms an angle, in relation to an axis parallel to a tangent to one of the concave and convex surfaces, that is too large to allow to an instrument for insertion of the cage between the vertebrae to fit onto the cage in an orientation that is more or less parallel to a tangent to one of the concave and convex surfaces. Thus, the orientation of the hole does not conform to the general curvature of the cage obtained by its convex and concave surfaces and does not allow an effective thrust to be applied to the cage on its axis of curvature. The cage, which is made fragile by this hole, is therefore in danger of breaking when pressure has to be applied at an angle that is too large in relation to the axis of curvature of the cage, which therefore proves difficult to implant by the transforaminal approach. Finally, withdrawal of the instrument inserted into the hole proves to be difficult due to the unsuitable orientation of the latter.

In this context, it is of interest to propose an intersomatic cage, preferably in a solid and sterile material, that has a shape and dimensions that make it suitable to be implanted through the transforaminal approach without an excessively large lesion of the articular processes, and having resources to fit onto an instrument for insertion of the cage between the vertebrae, with an orientation that conforms to the general shape of the cage. It is also of interest to propose an instrument for implanting the cage, and which is designed for the shapes and dimensions of the cage, allowing easy implantation of the cage between the vertebrae. Also known from prior art are previous designs of instruments for the implantation of intersomatic cages that have at least one rod designed to be inserted into a hole in the cage in order to hold the latter during passage through the foramen. However some of these instruments known from prior art require an ablation of at least one part of the articular processes impeding access to the foramen when the cage and the instrument have excessively large dimensions. Moreover, the transforaminal approach is relatively obstructed and is not perfectly straight. It is therefore desirable that the instrument should have an elbow (a curved or angled portion) at the end holding the cage. Some instruments known from prior art have dimensions that are small enough not to necessitate ablation of the articular processes, and some of these instruments have an angled portion that allows one to bypass the structure obstructing access to the disc space, but the rod designed to hold the cage, as well as the hole of the cage in which this rod is designed to be inserted, have an orientation that it not very compatible with the optimal thrust axis allowing insertion of the cage between the vertebrae and not very compatible with easy withdrawal of the rod when the cage has been implanted. It is therefore desirable to propose an instrument whose shape and dimensions are suitable for insertion using the transforaminal approach, having an angled portion to bypass the structures obstructing access to the disc space and having a rod designed to be inserted into a hole in the cage with an orientation that is optimal in order to facilitate the implantation of the cage between the vertebrae, and then withdrawal of the instrument.

SUMMARY

This present invention has as its objective to circumvent some disadvantages of the previous designs by proposing an intersomatic cage for an intervertebral fusion graft of suitable shape and of limited dimensions to be implanted through the transforaminal approach while also having adequate robustness to effectively maintain a disc space that allows the growth of the graft.

This objective is met by an intersomatic cage for an intervertebral fusion graft comprising a body generally defining an arc, the body comprising:
- a lateral concave surface;
- a lateral convex surface;
- a substantially transverse upper surface;
- a substantially transverse lower surface; an end wall at a first longitudinal extremity of the body, the end wall comprising an end hole configured to receive a retaining end of a rod of an implantation instrument and oriented substantially tangential to the arc defined by the body; and
- an incurvate return part at a second longitudinal extremity of the body opposite the end wall.

According to another feature, the end wall comprises a recess configured to receive a pin of an implantation instrument.

According to another feature, the return part comprises a return hole oriented substantially tangential to the arc defined by the body and configured to receive an end portion of an implantation instrument.

According to another feature, the end wall comprises a recess configured to receive a pin of an implantation instrument, the end hole, the recess, and the return hole being configured to cooperate with, respectively, a retaining end of a rod, a pin, and an end portion of an implantation instrument, to secure a grip on the intersomatic cage by the implantation instrument.

According to another feature, at least one of the upper and lower surfaces of the body comprises serrations oriented to oppose the movement of the intersomatic cage following intervertebral implantation of the intersomatic cage.

According to another feature, the return part comprises upper and lower surfaces extending, respectively, the upper and lower surfaces of the body, at least one of the upper and lower surfaces of the return part comprising serrations configured to oppose the movement of the intersomatic cage following intervertebral implantation of the intersomatic cage.

According to another feature, the return part comprises upper and lower surfaces extending, respectively, the upper and lower surfaces of the body, at least one of the upper and lower surfaces of the return part comprising a chamfer configured to facilitate the intervertebral implantation of the intersomatic cage.

According to another feature, the first and second longitudinal extremities of the body define a longitudinal axis of the intersomatic cage, and at least some of the serrations are oriented substantially parallel to the longitudinal axis of the intersomatic cage.

According to another feature, the first and second longitudinal extremities of the body define a longitudinal axis of the intersomatic cage, and at least some of the serrations are oriented substantially perpendicular to the longitudinal axis of the intersomatic cage.

According to another feature, the first and second longitudinal extremities of the body define a longitudinal axis of the intersomatic cage, and at least some of the serrations are disposed in a chevron configuration about an axis substantially perpendicular to the longitudinal axis of the intersomatic cage.

According to another feature, the first and second longitudinal extremities of the body define a longitudinal axis of the intersomatic cage, and at least some of the serrations define concentric circular arcs each being disposed symmetrically to the arc defined by the body, in relation to an axis of symmetry substantially parallel to the longitudinal axis of the intersomatic cage.

According to another feature, at least some of the serrations are oriented substantially normal to the arc defined by the body.

According to another feature, all of the serrations on the upper or lower surface of the intersomatic cage have substantially the same orientation.

According to another feature, some of the serrations on the upper or lower surface of the intersomatic cage do not have the same orientation as other serration on the same surface of the intersomatic cage.

According to another feature, serrations on each of the upper and lower surfaces of the intersomatic cage have the same orientation.

According to another feature, the serrations on the upper surface of the intersomatic cage have an orientation different from the orientation of the serrations on the lower surface of the intersomatic cage.

According to another feature, the body comprises a radio-opaque marker configured to identify the intersomatic cage in x-ray images.

According to another feature, the mean planes defined by the upper and lower surfaces of the cage are substantially parallel to each other.

According to another feature, the mean planes defined by the upper and lower surfaces of the cage form an angle allowing to correct defects of the spine.

According to another feature, at least one of the surfaces of the cage comprises at least one opening allowing the growth of a bony graft or substitute.

According to another feature, at least one slit passes through the body of the cage and forms a conduit extending form at least one of the surfaces of the cage to another, said slit being configured for receiving an anchor comprising a flat anchor plate intended to be impacted into a vertebral body with which the cage is in contact.

Another objective of this present invention is to propose an instrument for implanting an intersomatic cage between the vertebrae, facilitating access to the disc space and allowing a good grip to be obtained on the cage.

This objective is met by an instrument for the implantation of an intersomatic cage for an intervertebral fusion graft comprising a body generally defining an arc, the body comprising a lateral concave surface; a lateral convex surface; a substantially transverse upper surface; a substantially transverse lower surface; an end wall at a first longitudinal extremity of the body, the end wall comprising an end hole oriented substantially tangential to the arc defined by the body; said instrument comprising:
  a rod comprising a retaining end configured for insertion in the end hole;
  a gripping end for gripping the intersomatic cage, the gripping end comprising
    a support spatula comprising a base and generally defining an arc complementary to the arc defined by the body,
    a guide tube in which the rod is slidably disposed and to which the base of the support spatula is mounted, the guide tube comprising an opening through which the retaining end of the rod can transit for insertion in the end hole; and
  a handling end for manipulating the instrument.

According to another feature, the rod extends substantially to the vicinity of the handling end of the instrument.

According to another feature, the instrument comprises a button attached to the rod and a groove through which the button projects, the button being configured for sliding the rod to adjust the position of the retaining end of the rod in relation to the opening in the guide tube.

According to another feature, the guide tube comprises a pin configured to engage a recess disposed on the end wall of the intersomatic cage.

According to another feature, the support spatula comprises an end portion distal from the base, the end portion configured for insertion into a return hole disposed on an incurvate return part of the intersomatic cage, which return hole is oriented substantially tangential to the arc defined by the body.

According to another feature, the guide tube comprises a pin configured to engage a recess disposed on the end wall of the intersomatic cage, the retaining end of the rod, the pin, and the end portion of the implantation instrument being configured to cooperate with, respectively, the end hole, the recess, and the return hole, to secure a grip on the intersomatic cage by the implantation instrument, and to facilitate the withdrawal of the instrument following implantation of the intersomatic cage by removing the retaining end of the rod from the end hole.

According to another feature, the instrument further comprises an aiming tube that extends substantially to the vicinity of the handling end of the instrument, wherein the guide tube comprises a mobile portion that pivots in relation to the aiming tube at least in a primary pivot direction, the primary pivot direction lying substantially within a plane in which the arc defined by the support spatula lies, and the position of the mobile portion in relation to the aiming tube defining a pivot angle.

According to another feature, one of the mobile portion or the aiming tube comprises a substantially spherical end, and the other of the mobile portion or the aiming tube comprises a recessed end having a shape and dimensions complementary to the shape and dimensions of the spherical end, the spherical end and the recessed end being configured, respectively, as a ball component and a socket component of a ball and socket connection.

According to another feature, the socket component comprises opening edge portions, one of which portions is proximal to the support spatula and is configured to encompass the ball component less than the other opening edge portions to allow further pivoting of the mobile portion in relation to the aiming tube at least in the primary pivot direction.

According to another feature, the rod is flexible and slidably transits the ball and socket connection through a channel located at the centre of the ball component and the socket component, the channel having a hollowed portion proximal to the support spatula, the hollowed portion configured to allow the rod to slide through the ball and socket connection even when the mobile portion is pivoted in relation to the aiming tube.

According to another feature, the instrument further comprising a lock slidably disposed along the aiming tube, the lock having a forward position and being configured to fix the mobile portion of the guide tube at a selected pivot angle when the lock is disposed in the forward position.

According to another feature, the mobile portion comprises a serration configured to increase the maximum pivot angle at which the mobile portion of the guide tube can be fixed by the lock and to provide a pre-determined pivot angle.

According to another feature, the serration is configured for engagement with the lock without disposing the lock in the forward position, said engagement establishing a pre-determined pivot angle and preventing pivoting of the mobile portion.

According to another feature, the handling end of the instrument comprises a handle configured to allow the manipulation of the instrument and to facilitate the implantation of the intersomatic cage between the vertebrae.

Another objective of the preset invention is to propose a method for implanting a transforaminal intersomatic cage according to the invention into the disc space with an instrument according to the invention.

This objective is reached by a method for implanting an intersomatic cage for an intervertebral fusion graft into the disc space between adjacent vertebrae of a vertebral column, said disc space comprising an annulus and a nucleus, said method comprising the steps of:
  providing an intersomatic cage for an intervertebral fusion graft comprising a body generally defining an arc, the body comprising:
    a lateral concave surface,
    a lateral convex surface,
    a substantially transverse upper surface,
    a substantially transverse lower surface,
    an end wall at a first longitudinal extremity of the body, the end wall comprising an end hole configured to receive a retaining end of a rod of an implantation instrument and oriented substantially tangential to the arc defined by the body, and
    an incurvate return part at a second longitudinal extremity of the body opposite the end wall, the return part comprising a return hole oriented substantially tangential to the arc defined by the body and configured to receive an end portion of an implantation instrument;
  providing an instrument comprising:
    a rod comprising a retaining end configured for insertion in the end hole, a gripping end for gripping the intersomatic cage, the gripping end comprising a support spatula comprising a base and generally defining an arc complementary to the arc defined by the body, the support spatula comprising an end portion distal from the base configured for insertion into the return hole of the intersomatic cage, and a guide tube in which the rod is slidably disposed and to which the base of the support spatula is mounted, the guide tube comprising an opening through which the retaining end of the rod can transit for insertion in the end hole, and a handling end for manipulating the instrument;

making an incision to access the vertebral column;

incising the annulus and removing the nucleus from the disc space;

inserting the end portion of the spatula into the return hole of the intersomatic cage;

disposing the arc defined by the body proximal to the arc defined by the spatula;

fixing the intersomatic cage onto the instrument by inserting the retaining end of the rod into the end hole;

disposing the intersomatic cage in the disc space in an arcing movement;

releasing the intersomatic cage from the instrument by removing the retaining end of the rod from the end hole;

removing the instrument from the disc space; and suturing the annulus and the skin.

According to another feature, the step of disposing the intersomatic cage in the disc space is preceded or accompanied by a step of articulating a mobile portion of the instrument to a selected angle, said step of articulating the mobile portion being followed by a step of locking the mobile portion at the selected angle.

According to another feature, the step of disposing the intersomatic cage in the disc space is followed by the steps of determining the position and orientation of the intersomatic cage in the disc space by detecting a radio-opaque marker comprised in the body of the intersomatic cage with x-rays and, if such position or orientation is improper, adjusting the position or orientation of the intersomatic cage in the disc space.

According to another feature, the steps of inserting the end portion of the spatula into the return hole of the intersomatic cage and disposing the arc defined by the body proximal to the arc defined by the spatula are followed by, and the step of fixing the intersomatic cage onto the instrument by inserting the retaining end of the rod into the end hole is preceded by, a step of engaging a pin of the instrument with a recess disposed on the end wall of the intersomatic cage.

According to another feature, the step of disposing the intersomatic cage in the disc space is preceded by a step of distraction of the adjacent vertebrae.

BRIEF DESCRIPTION OF THE DRAWINGS

Other features and advantages of this present invention will appear more clearly on reading the description that follows, provided with reference to the appended drawings, in which:

FIG. 3A provides a top view of one embodiment of the instrument for implanting an intersomatic cage with a plane section 3B-3B, with FIG. 3B showing a view in section according to axis 3B-3B of this embodiment of the insertion instrument, and FIGS. 3C and 3D showing the detail of the portions indicated, respectively, by circles 3C and 3D in FIG. 3B;

DETAILED DESCRIPTION OF THE EMBODIMENTS

Figure 1A:
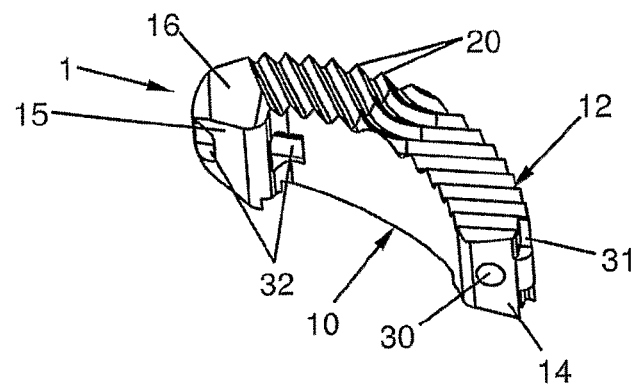
FIGS. 1A, 1B, 1C and 1D are views in perspective of the intersomatic cage according to various embodiments of the invention.

This present invention concerns a transforaminal intersomatic cage for an intervertebral fusion graft. This cage is used to maintain a disc space that is sufficient to allow a graft to be inserted into the disc space in order to grow and to allow an osseous fusion (arthrodesis) of the adjacent vertebrae. This cage is called transforaminal since it is particularly suitable to be implanted through the transforaminal approach, although it can also be implanted by any approach to suit the convenience of the surgeon responsible for the implantation. In a manner which is already known, this intersomatic cage has a body (1) in the shape of a circular arc having a lateral concave surface (10), a lateral convex surface (11), a straight upper surface (12), and a straight lower surface (13). The body (1) therefore has more or less the shape of a banana or simple bracket, and therefore does indeed describe a circular arc.

This circular arc shape of the cage according to various embodiments of the invention is particularly well-matched to the shape of the edges of the vertebral plates, which allows the cage to be positioned in the vicinity of the periphery of the vertebral plates, that is to say on their most solid portion. A cage according to various embodiments the invention will therefore be implanted at the level of the anterior peripheral portion of the vertebral plates, for example. This positioning of the cage close to the edges of the vertebral plates also enables to obtain a large initial surface for an osseous graft or a substitute. At one of the extremities of the body (1), the cage includes an end wall (14) having at least one hole (30), called the end hole, designed to receive a rod (53) of an instrument (5) for implantation of the cage between the vertebrae.

In a particularly advantageous embodiment of the cage according to the invention, the end hole (30) has an orientation that is more or less tangential to the circular arc described by the body (1). This orientation of the end hole (30) tangentially to the circular arc described by the body (1) facilitates the thrusting of the cage by the cage implantation instrument (5) and facilitates the insertion and withdrawal of the rod (53) of this instrument (5), respectively, into and out of the end hole (30). Moreover, this end wall (14) includes at least one recess (31) designed to receive at least one pin (54) of a cage implantation instrument (5). This recess (31) is used to provide an additional surface for the gripping of the cage by the instrument. It can consist of a simple shoulder or a recess of more complex shape such as, for example, a recess with a groove in which a serration of the pin (54) (thus having the shape of a spur, for example) of the instrument (5) can be locked.

In a particularly advantageous embodiment of the cage according to the invention, the extremity opposite to the end wall (14) of the body (1) includes a return part (15) extending the body (1) toward the centre of the circle on which the circular arc described by the body (1) lies. This return part provides better stability of the intersomatic cage between the vertebrae without increasing its dimensions excessively. This return part is used to prevent the intersomatic cage from tilting to one of its sides under the effect of the stresses to which it is subjected when implanted between two vertebrae of a patient. Moreover, this return part (15) includes at least one hole (32), called the return hole, whose orientation is more or less tangential to a circular arc defined by the concave surface (10) of the body (1) and designed to receive at least one end portion (55) of a cage implantation instrument (5). Thus, the instrument (5) can include a spatula (56) having a shape complementary to that of the circular arc described by the body. This spatula (56) thus hugs the shape of the cage by fitting its body (1). At one end of the spatula (56), an end portion (55) can be designed for insertion into this return hole (32). The fitting together of the end hole (30), the recess (31) and the return hole (32) with the rod (53), the pin (54) and the end portion (55) of the cage implantation instrument (5) respectively, ensures a good grip on the cage by the instrument (5) when one end of the rod (53) is placed in the end hole (30). This complete gripping of the cage up to the most distal end facilitates the implantation of the cage by providing good stability of the cage at the end of the instrument (5). This good stability is also particularly important in the case of implantation through the transforaminal approach. The rod (53) is designed to slide in the instrument (5) so that it can be withdrawn from the end hole (30) and to allow freeing of the cage and withdrawal of the instrument (5).

Figure 1B:
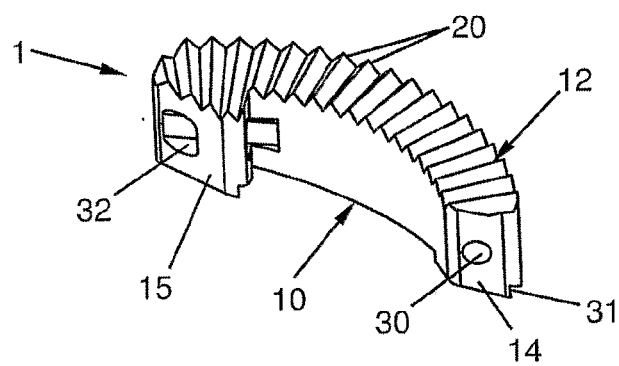
Figure 1C:
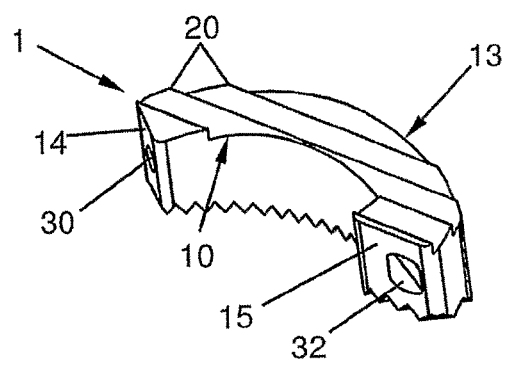
Figure 1D:
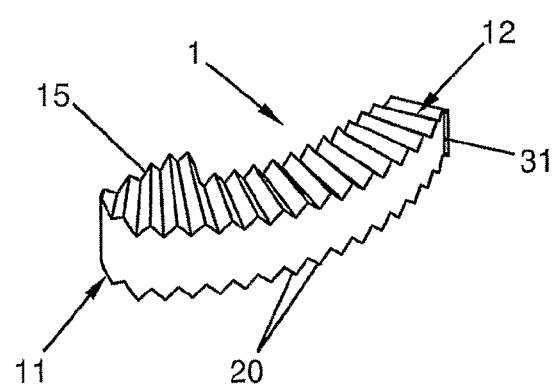

In a manner which is already known, at least one of the upper and lower surfaces of the body (1) is equipped with serrations (20) that oppose the movement of the cage in relation to the adjacent vertebrae between which it is implanted. The invention provides for different possible orientations of the serrations (20). In an advantageous manner, in one embodiment of the invention, the serrations (20) present on two opposite surfaces of the cage may not have the same orientation, so as to oppose the movement of the cage in different directions for each of the faces, as can be seen particularly in FIGS. 1A to 1C. In another embodiment, the serrations (20) present on two opposite surfaces of the cage will have the same orientation, as can be seen particularly in FIG. 1D. Likewise, serrations (20) present on one surface of the cage can have an orientation that is different from other serrations located on the same surface. Conversely, all the serrations (20) present on a given surface of the cage can have the same orientation. Depending on the embodiment, the intersomatic cage can therefore include any combination of these orientations on all or part of either of its surfaces. The extremities of the circular arc described by the body (1) define a longitudinal axis of the cage. The cage has larger dimensions on this longitudinal axis than on the axis perpendicular to it. This longitudinal axis will allow the different possible orientations of the serrations to be defined. Thus in one embodiment, at least one part of the serrations (20) can be oriented parallel, as can be seen particularly in FIG. 1C, or perpendicular to this longitudinal axis of the cage. In another embodiment, they can be oriented so as to form an angle of between 0 and 90 degrees in relation to this longitudinal axis of the cage. In another embodiment, at least one part of the serrations (20) can describe chevrons that are centred in relation to an axis perpendicular to this longitudinal axis, as can be seen particularly in FIG. 1A. In another embodiment, at least one part of the serrations (20) can describe concentric circular arcs, each with, in relation to the circular arc described by the body (1), an axial symmetry whose axis of symmetry is parallel to this longitudinal axis of the cage. In another embodiment, at least one part of the serrations (20) will be oriented parallel to radii defined by the circle on which the circular arc described by the body lies (1), as can be seen particularly in FIGS. 1B and 1D.

Furthermore, the return part (15) includes upper and lower surfaces extending the upper and lower surfaces respectively of the body (1). In one embodiment, at least one of these upper and lower surfaces of the return part (15) can also be equipped with serrations (20) that oppose the movement of the cage. In another embodiment, at least one of these upper and lower surfaces of the return part (15) can include at least one chamfer (16) facilitating the insertion of the cage in the disc space, as can be seen particularly in FIG. 1A.

In the embodiments shown in the figures, the upper and lower surfaces of the cage (1) are generally flat and the mean planes defined by these upper and lower surfaces are substantially parallel to each other. In some embodiments (not shown) of the present invention, the mean planes defined by the upper and lower surfaces of the cage (1) are not parallel to each other. These planes may thus form an angle allowing to correct defects of the spine (orientation of the vertebrae). In such embodiments, the cage (1) can impose a lordosis when implanting between the vertebrae. Since several cages (1) can be used together within a single intervertebral space, such embodiments allow correcting defects of the spine in any orientation, because any combination of cages (1) with different angles between their upper and lower surfaces can be used.

Figure 5A:
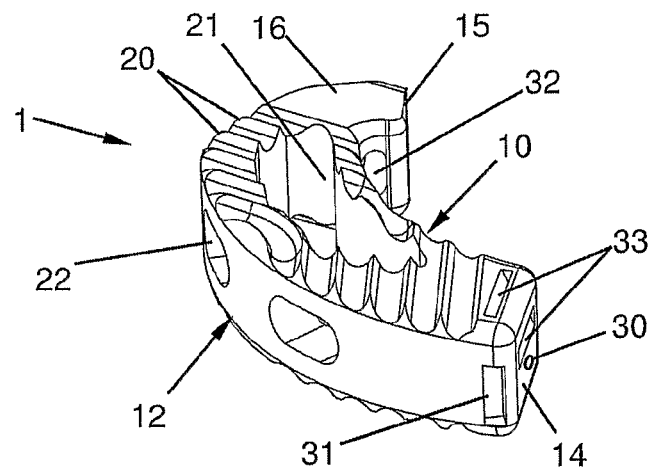
FIGS. 5A and 5B provide views in perspective of two different embodiments of the intersomatic cage according to the invention and FIG. 5C provides a top view of another embodiment of the intersomatic cage according to the invention.
Figure 5B:
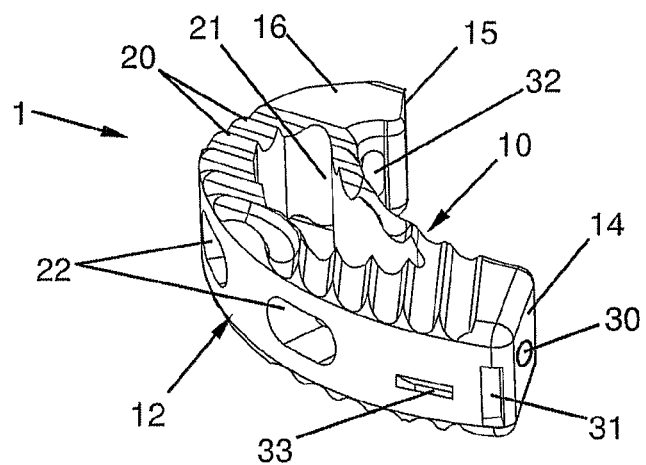
Figure 5C:
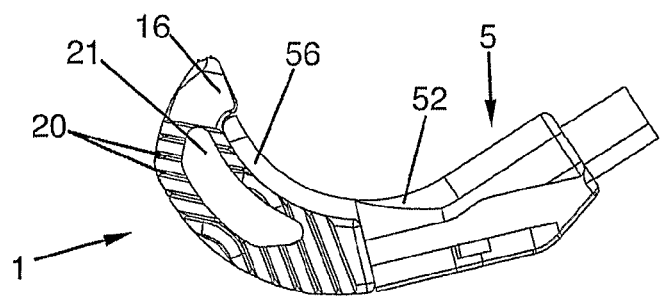
Figure 6A:
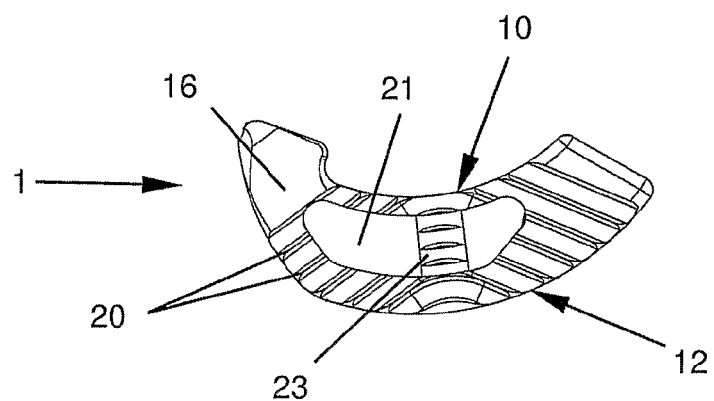
FIG. 6A provides a top view of another embodiment of the intersomatic cage according to the invention and FIGS. 6B and 6C provide, respectively, a top view and a side view, of an anchor according to another embodiment of the present invention.

In some embodiments of the present invention, as particularly shown in FIGS. 5A to 5C and 6A, at least one of the surfaces of the cage comprises at least one opening (21 or 22). As shown on the figures, the cage (1) can comprise such openings (21) located on its upper and/or lower surfaces and can also comprise such openings (22) on at least one of its side surfaces (10, 12). In various embodiments, such opening (21, 22) may form a blind hole or may form a conduit through the body of the cage. Such openings allow securing the cage onto the vertebrae by enabling a bony graft or substitute to grow inside the opening. The bony graft or substitute may thus be inserted inside the opening (21 or 22) or may be simply placed in the intervertebral space and grow inside the opening. In particular when the cage comprises an opening (21) forming a conduit extending from the upper surface to the lower surface, it can be advantageous that the cage (1) further comprises a crosspiece (23) passing through the opening (21) for consolidating the cage (1), as shown in FIG. 6A.

Figure 6B:
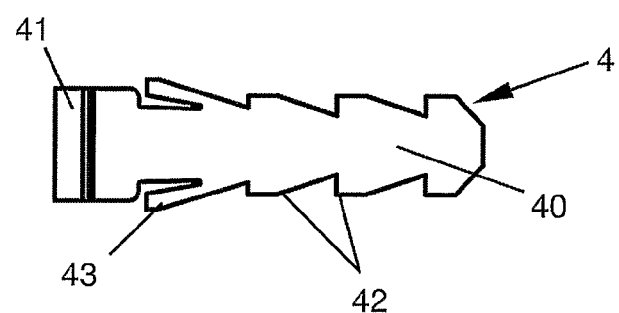
Figure 6C:
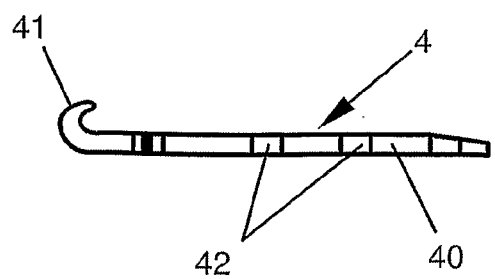

In some embodiments of the present invention, the cage comprises at least one slit (33) passing through the body of the cage (1) and extending form at least one of the surfaces of the cage to another, that is to say the upper surface and/or lower surface and/or the end wall and/or the concave surface (10) and/or the convex surface (12) and/or one surface of the return part (15). As shown in FIG. 5A, the slit (33) may, for example, extend form the end wall (14) to the upper surface of the cage but may extend from the convex surface (12) to the lower surface of the cage as shown in FIG. 5B. This slit (33) is intended to receive an anchor (4), intended to be impacted into the vertebral bodies. As shown in FIGS. 6B and 6C, the anchor (4) comprises a substantially rectangular flat plate (40) intended to enter the slit (33) and be impacted in the vertebral body, thus enabling the anchoring of the cage (1) in the vertebra. The slit (33) is thus a conduit through the body of the cage (1) and may have a rectangular section adapted to receive the anchor (4). The anchor plate (40) can comprise notches (42) oriented to retain the anchor (4) in a vertebra. In a variant embodiment, the anchor plate (40) can comprise at one of its end, a chamfer or bevel (visible in FIG. 6C) for facilitating its penetration into the vertebral bodies. In a variant embodiment, at the end opposite the end that may comprise the chamfer, the anchor plate (4) may comprises a return part (41) for securing the anchor onto the cage (1). This return part (41) may consist in a curved section, as shown in FIG. 6C, which may be interlocked onto an edge of the opening of the slit (33) on one surface of the body. In a variant embodiment, the edge of the slit (33) may comprise a groove for facilitating the interlocking of the return part (41) of the anchor (4). In a variant embodiment, the anchor (4) comprises, close to the return part (41), flexible tabs (43) oriented towards the return part (41) of the anchor (4). In this variant, these flexible tabs (43) are configured to fold back against the edges of the anchor plate (40) to permit the insertion of the anchor (4) into the slit (33) of the cage (1). In this embodiment of the anchor (4), the inner walls of the slit (33) of the cage (1) comprise recesses for receiving the flexible tabs (43) and securing the anchor (4) into the cage (1). In this embodiment, the return part (41) of the anchor (4) may consist simply, for example, in an enlargement of the anchor plate (40) forming a stop cooperating with the surface of the cage on which the slit is located. Depending on the embodiment chosen, the orientation of the slit (33), and thus of the anchor (4) inserted in it, may form an angle between 5° and 85° relative to the upper or lower surface of the cage. The cage (1) may comprise several slits (33) for the insertion of several anchors (4), with similar or different angles. Furthermore, the various embodiments of the slits (33) and anchors (4) described here can used in any embodiment of the cage (1), irrespective of its shape (angle between the upper and lower surfaces) or the presence or absence of openings (21 and/or 22).

This present invention also concerns an instrument (5) for the implantation of an intersomatic cage between the vertebrae. This instrument according to the invention is particularly suitable for implantation, through the transforaminal approach, of an intersomatic cage for an intervertebral fusion graft, although it could naturally be used for any approach that is convenient for the surgeon responsible for the implantation. The instrument (5) is designed to be particularly suitable for use in combination with the intersomatic cage described previously. The instrument (5) according to an embodiment of the invention includes an extremity for gripping the cage allowing the cage to be held at the end of the instrument and called the gripping end. The extremity of the instrument opposite its gripping end allows the manipulation of the instrument by the surgeon and is called the handling end. The gripping end of the instrument (5) includes at least one tube (52), called the guide tube. At the extremity of this guide tube (52), on one edge of the latter, is mounted a spatula (56), called the support spatula. This spatula (56) has the shape of a circular arc, designed to at least partially fit onto the circular arc described by the body (1) of the cage. By hugging the shape of the body (1), this spatula provides the cage with solidity. The spatula will therefore protect the cage in particular against impact, to which it is sometimes less resistant than to pressures. At the base of the support spatula (56), the guide tube (52) includes an opening through which one end of the rod (53) passes to fit into the end hole (30) of the cage. This rod (53) is mounted to slide in the guide tube (52) and has a shape and dimensions that make it suitable to be inserted into the end hole (30) of the cage, so as to allow the cage to be gripped. In one embodiment, this rod (53) extends up to the vicinity of the handling end of the instrument (5). The rod (53) includes at least one button (61) projecting through a groove (610) on at least one edge of the instrument (5), this button (61) allowing the rod to be slid (53) and its position to be adjusted in relation to the opening present at the end of the guide tube (52) holding the support spatula (56). This button will preferably be located at the extremity of the rod (53) and, according to the embodiment, can therefore be located close to the handling end of the instrument (5) or anywhere on the instrument, although it would obviously be more practical, in principle, that it should be close to the handling end.

In one embodiment, the guide tube (52), at the end on which the support spatula is mounted (56) but on the opposite edge, includes at least one pin (54) whose shape and dimensions are suitable to fit onto at least one recess (31) present on the end wall (14) of the cage. This embodiment is particularly suitable for the one of the embodiments of the cage presented above and improves the quality of the grip on the cage by the instrument (5).

In one embodiment, the support spatula (56), at the end opposite to the guide tube (52), includes at least one end portion (55) whose shape and dimensions make it suitable to be inserted into at least one hole (32), called the return hole, present on a return part (15) of the cage. This embodiment is particularly suitable for the one of the embodiments of the cage in which a return part (15) extends the body (1) toward the centre of the circle on which the circular arc described by the body (1) lies. Since this return hole (32) has an orientation that is more or less tangential to a circular arc defined by the concave surface (10) of the body (1), the end portion (55) at the end of the spatula (56) in a circular arc will therefore have a shape that is particularly suitable to fit into the return hole (32). In one embodiment that combines the resources for fitting together the instrument and the cage, described above, with the fitting together of the rod (53), the pin (54) and the end portion (55) of the cage implantation instrument (5) to the end hole (30), the recess (31) and the return hole (32) respectively of the cage, ensures a good grip on the cage by the instrument (5) when one end of the rod (53) is placed in the end hole (30), and facilitates the implantation of the cage.

In a particularly advantageous embodiment and suitable for the transforaminal approach, the guide tube (52), at the end opposite to that holding the support spatula (56), includes a mobile portion (57) that pivots in relation to a tube (59), called the aiming tube, extending up close to the handling end of the instrument (5). This mobile portion (57) pivots in at least one direction that is more or less parallel to the orientation of the circular arc defined by the support spatula (56). As can be seen particularly in FIG. 3C, the mobile portion (57) and the aiming tube (59) together can form a ball and socket connection (or swivel link), one of them having one end in the form of a ball or sphere (592) and the other having a hollow end forming a socket, called spherical recess (571), whose shape and dimensions are complementary to those of this sphere. In the embodiment illustrated in FIG. 3C, one end of the aiming tube (59) has a shape of sphere (592) and the corresponding end of the guide tube (52) forms a spherical recess. In one embodiment of the invention, at least the edge (575) of the spherical recess (571) located on the same side of the instrument (5) as the support spatula (56), in the ball and socket connection formed by the mobile portion (57) and the aiming tube (59), encompasses the sphere to a lesser extent than the other edges (576) of this recess (571), so as to allow pivoting at least in a direction that is more or less parallel to the orientation of the circular arc defined by the support spatula (56).

Figure 2A:
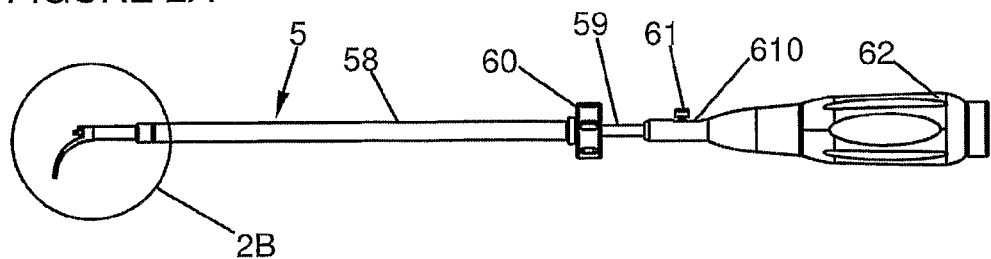
FIGS. 2A and 2C are views in profile of one embodiment of the instrument for implanting intersomatic cage between the vertebrae, with the gripping end of the instrument in position, respectively straight and angled, with FIGS. 2B and 2D showing the detail of the portions indicated by circles 2B and 2D respectively in FIGS. 2A and 2C respectively.
Figure 2B:
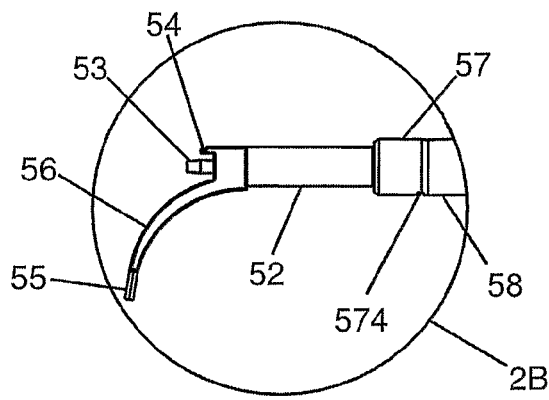
Figure 2C:
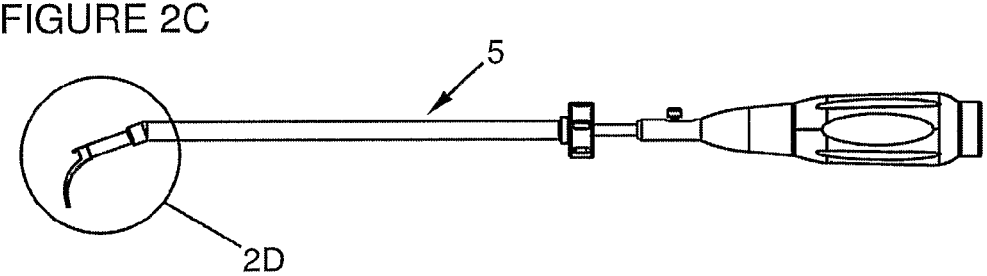
Figure 2D:
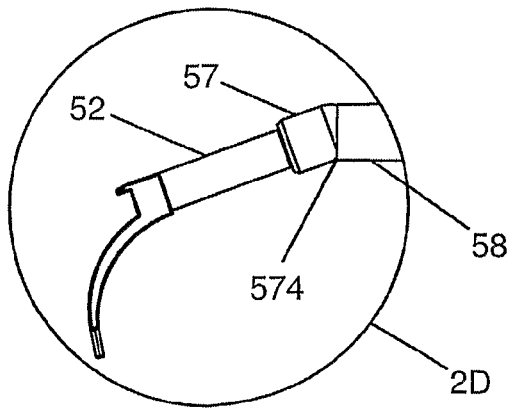
Figure 4A:
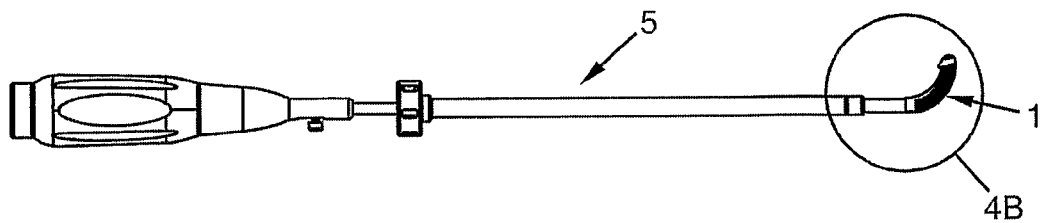
FIG. 4A provides a view in profile of one embodiment of the instrument for implanting an intersomatic cage with a method for insertion of the intersomatic cage held at the gripping end of the instrument, with FIG. 4B showing the detail of the portion indicated by circle 4B in FIG. 4A, and FIG. 4C showing a top view of this embodiment of the instrument holding the intersomatic cage, with a plane section 4D-4D, where FIG. 4D provides a view in section according to axis 4D-4D of this embodiment.
Figure 4B:
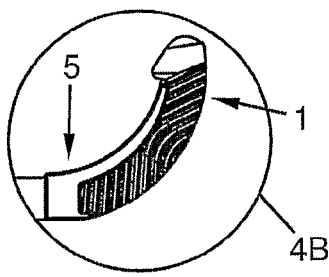
FIG. 4E shows the detail of the portion indicated by circle 4E in FIG. 4D.
Figure 4C:
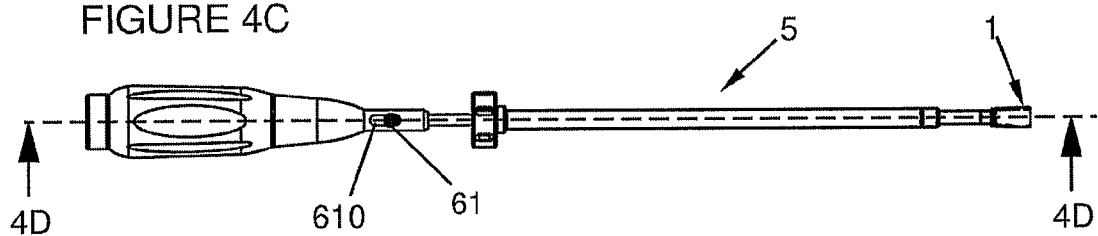
Figure 4D:
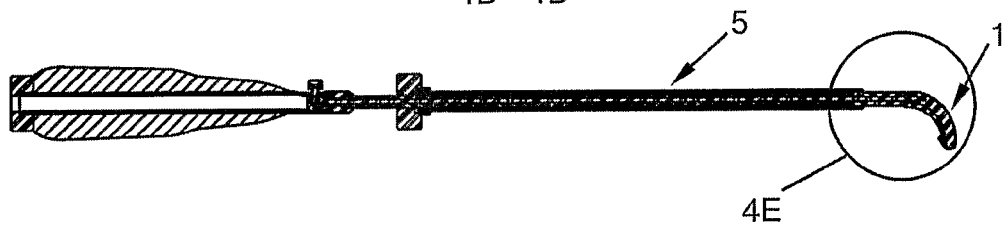
Figure 4E:
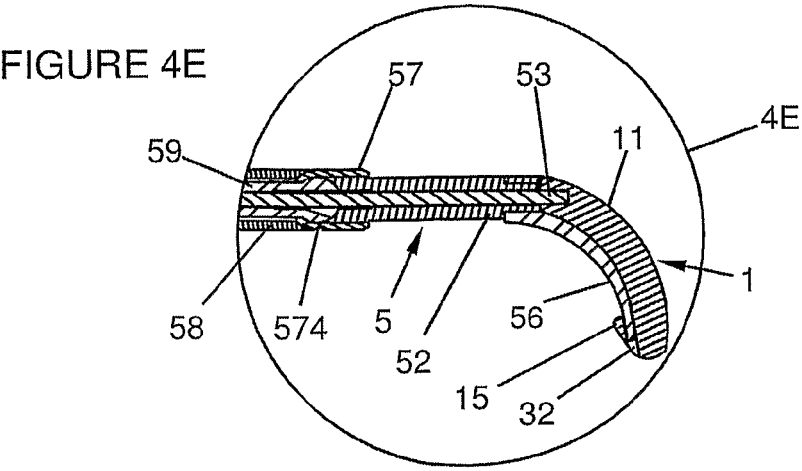

In one embodiment, the rod (53) is flexible, and traverses the ball and socket connection at its centre. The sphere (592) then has a channel at its centre to allow the rod to slide (53). This channel will be hollowed out at least on its edge located on the same side of the instrument (5) as the support spatula (56). Thus, the channel will include a hollowed out portion (593) allowing the rod (53) to slide through the ball and socket connection even when the instrument (5) is in its angled position due to pivoting of the ball and socket connection, as illustrated in FIGS. 2C and 2D.

In one embodiment, a locking tube (58) is screwed onto the aiming tube (59) and includes a locking ring (60) that allows the locking tube to be screwed in (58). Screwing-in and unscrewing allows the forward and backward motion of the locking tube (58) in relation to the aiming tube (59). The forward motion of the locking tube (58) results naturally in bringing the locking tube (58) into contact with the mobile portion (57) and, as a consequence, prevents the pivoting of the mobile portion (57). Thus, the guide tube (52) can be locked in relation to the aiming tube (59), at any angle between the guide tube (52) and the aiming tube (59). The mobile portion (57) that pivots in relation to the aiming tube (59) can also, in one embodiment, include at least one serration (574), particularly visible in FIG. 3C. The presence of this serration (574) allows pivoting of the mobile portion (57) through a larger amplitude than if the mobile portion entered directly into contact with the locking tube (58). This serration (574) allows to obtain a particular angle formed by the angled portion between the support tube (52) and the aiming tube (59). Moreover, in one embodiment, this serration (574) can be designed so that when the guide tube (52) forms a given angle with the aiming tube (59), one edge of one end of the locking tube (58) locks into this serration (574), as illustrated in FIGS. 2A to 2D. This serration (574) is therefore used to stop the pivoting and to maintain the instrument in at least one position until it is totally immobilised by screwing-in of the locking tube (58).

In a manner which is already known, the handling end of the instrument (5) can naturally be fitted with a handle (62) allowing the manipulation of the instrument (5) and facilitating the implantation of the cage between the vertebrae by allowing effective thrust to be applied to the instrument (5).

As mentioned previously, the intersomatic cage and the instrument according to this present invention are particularly suitable for implantation of the cage between two adjacent vertebrae using the transforaminal approach. This implantation can be performed as described below, although other procedural variants can naturally exist, and the surgeon can naturally adapt the technique described here at his convenience, in accordance with any changes in the techniques employed conventionally for example. In particular, this present invention can be used in combination with osseous anchor implants, connected together by immobilising bars, allowing the movement of the two adjacent vertebrae, between which the cage is designed to be inserted, to be eliminated or limited. These osseous anchor implants can consist, for example, of those described in the international patent applications submitted by this present applicant and published under the numbers WO02/080788(A1), WO03/049629(A1) and WO2005/020829(A1) or by any other type of resources for immobilisation of the adjacent vertebrae. The procedure relating to the joining of the adjacent vertebrae is specific to the resources used to immobilise the adjacent vertebrae and therefore need not be described here.

Only the procedure used during an implantation through the transforaminal approach will be detailed here, the implantation by other approaches being relatively similar but easier, in particular because of the fact that the transforaminal approach needs to bypass the articular processes. The procedure for implantation through the transforaminal approach begins naturally by at least one incision laterally to the axis of the vertebral column. Preferably, two intermuscular incisions will be made, along a path that is well known to the professional surgeon for example, as described by Dr Wiltse. According to the size of the cage chosen and/or according to the space between the two vertebrae, a resection, at least partial, of the articular processes can be effected in order to improve access to the foramen and to the disc space. These articular processes will then preferably be resected laterally, on the side for insertion of the cage. If an intra-articular graft is desired, an opening and an avivement (withdrawal of the cartilage) of the articular processes, at least on one side but possibly on both sides, will allow the insertion of at least one intra-articular graft. The insertion of the osseous anchor implants designed to immobilise the two adjacent vertebrae can be effected at this stage of the procedure. These osseous anchor implants screwed into each of the adjacent vertebrae and connected together by a bar, here allow a first posterior distraction in order to facilitate access to the disc space. A tool of known type such as a nerve root retractor (or root spreader) can be used to protect the roots of the vertebrae. A lateral incision in the external layer of the annulus, between the transverse articular processes for example, will provide access to the disc space. In a manner which is already familiar, the formation of an open flap, held by suspension ties for example, will facilitate the following operations. Then the surgeon will proceed to the complete removal of the nucleus and of the internal layers of the annulus. Different tools of known types, such as an angled disc clamp, curettes and rasps (straight and angled) will be used at this stage to prepare the disc space and withdraw the cartilage from the vertebral plates without damaging or weakening it.

At this stage of the procedure, the surgeon will have cleared access to the disc space. The osseous anchor implants will allow the surgeon to spread the vertebrae so as to facilitate insertion of the cage. For example, the surgeon will use osseous anchor implants screwed into the vertebrae and connected together by a bar parallel to the axis of the vertebral column. The osseous anchor implants generally include screws driven into the vertebrae and defining a longitudinal securing axis. At this stage, these longitudinal axes of the osseous anchor implants are not parallel to each other but cross in front of the vertebral column. Together with the axis of the bar, these axes form an inverted capital A. The surgeon will then adjust the spread of the osseous anchor implants. To this end, the surgeon can position spreader tubes on the heads of the osseous anchor implants in order to spread these as much as possible or can use distraction forceps of a known type, for example. In the case of osseous anchor implants having a mobile head (called polyaxial head), as disclosed, for example, in the patent application number WO2005/020829(A1), the surgeon will then screw in the head of these osseous anchor resources on the bar to fix their position along the bar parallel to the axis of the vertebral column. The osseous anchor implants thus implanted and held securely on the bar will allow an anterior distraction to be performed, thanks to the mobility of the head in relation to the bar. The surgeon applies pressure to the spreader tubes so as to move them toward each other, which tends to open the inverted capital A at its base, so that it becomes a capital H. In the case of osseous anchor implants having a fixed head, as disclosed, for example, in the patent application number WO03/049629(A1), the surgeon will use the distraction forceps to maintain the gap between the osseous anchor implants without screwing in the head of these osseous anchor resources on the bar. Even if the bar is fixed with a fixation screw having a ball and socket connection at its base, as disclosed in the application WO03/049629(A1), such screwing in would indeed result in blocking the head of the osseous anchor implants on the bar. The surgeon thus should rather maintain the gap between the osseous anchor implants with distraction forceps placed between the heads of the two osseous anchor implants screwed in each of the vertebrae. Then, The surgeon applies pressure to the spreader tubes so as to move them toward each other, which tends to open the inverted capital A at its base, so that it becomes a capital H because of, the presence of the distraction forceps. This operation can possibly be repeated several times. For example, in the case of osseous anchor implants with polyaxial head, the operation may be repeated by unscrewing the heads of the osseous anchor implants from the bar and separating the spreader tubes to spread the heads and then screwing in the heads of the implants and drawing together the spreader tubes to spread the feet of the capital H, thus opening the disc at the front. This anterior opening of the disc space can be accompanied by an adjustment of the lordosis.

The surgeon will then proceed to the choice of the cage to be implanted, using trial cages with the same dimensions as the cages designed to be implanted. A trial cage is placed on the instrument (5) and is then impacted into the disc space. Impaction should be effected without excessive force in order not to weaken (damage) the vertebral plates. The trial cage is removed using a tool of known type such as an extraction masselotte (or extractor or removal masselotte or bobweight), and this operation can be repeated until a cage of satisfactory size has been found.

The definitive cage can then be placed on the implantation instrument (5) by inserting the end portion (55) of the spatula (56) into the return hole (32) of the cage and moving the circular arc of the body (1) in relation to the spatula (56) until the pin (54) locks into the recess (31) of the end wall (14). The cage is then locked onto the instrument (5) by means of the sliding rod (53) which enters into the end hole (30). Articulation of the instrument at its distal part by means of the mobile portion (57) allows the most appropriate angle to be found for engagement of the cage in the intersomatic space. The angle can be locked by the screwing in the locking tube (58) using the threaded ring (60) for example by means of a tool of known type such as a pin wrench. The cage thus held on the instrument and oriented in an optimal manner can then be impacted between the vertebrae. The cage will preferably be impacted as anteriorly as possible, in a circular movement. In order to optimise the positioning of the cage, the angle of the articulation formed by the mobile part (57) can be adjusted during impaction, taking care to correctly lock this angle by means of the locking ring (60). The position and the orientation of the cage in the intersomatic disc space can then be verified by means of an x-ray appliance of known type, such as a brightness amplifier for example. In fact, in one embodiment the cage includes at least one radio-opaque marker which will be detected by the brightness amplifier. The surgeon can then adjust the positioning of the cage according to the position and the orientation of the marker or markers. When the cage has been correctly implanted, it will be released from the instrument (5) by moving the sliding rod (53) in the direction of the handling end. The surgeon then only has to position the osseous graft(s) or substitute(s) between the cage (preferably placed at the level of the anterior edges of the vertebral plates) and the medulary cavity. To this end, the surgeon will use a tool of known type, such as a spatula for example. The flap formed in the external layer of the annulus can then be re-closed and sutured, so as to maintain the graft in place. A graft, of the posterolateral type for example, can be effected at this stage in order to optimise the joining together of the vertebrae. Graft will be then placed on the transverse articular process for example. A redon drain can possibly then be put in place, and a subcutaneous suturing followed by a cutaneous suturing of the incisions will allow the surgical procedure to be finalised.

It should be obvious to people well versed in these techniques that this present invention allows embodiments in many other specific forms without the moving outside the spirit and scope of the invention as claimed and that it allows any combination of non-exclusive embodiments enclosed herein. As a consequence, the present embodiments should be considered as illustrations only, but can be modified within the domain defined by the reach of the attached claims, and the invention must not be limited to the details given above.

The invention claimed is:

1. An instrument for the implantation of an intersomatic cage for an intervertebral fusion graft comprising a body generally defining an arc, the body comprising a lateral concave surface; a lateral convex surface; a substantially transverse upper surface; a substantially transverse lower surface; an end wall at a first longitudinal extremity of the body, the end wall comprising an end hole oriented substantially tangential to the arc defined by the body; said instrument comprising:
   a rod comprising a retaining end configured for insertion in the end hole;
   a gripping end for gripping the intersomatic cage, the gripping end comprising a support spatula comprising:
   a base and generally defining an arc complementary to the arc defined by the body,
   a guide tube in which the rod is slidably disposed and to which the base of the support spatula is mounted, the guide tube comprising an opening through which the retaining end of the rod can transit for insertion in the end hole; and a handling end for manipulating the instrument, wherein the support spatula is configured to engage the intersomatic cage along the lateral concave surface, and wherein the support spatula comprises an end portion distal from the base, the end portion configured for insertion into a return hole disposed on an incurvate return part of the intersomatic cage, which return hole is oriented substantially tangential to the arc defined by the body.

2. An instrument according to claim 1, wherein the rod extends substantially to the vicinity of the handling end of the instrument.

3. An instrument according to claim 1, wherein the instrument comprises a button attached to the rod and a groove through which the button projects, the button being configured for sliding the rod to adjust the position of the retaining end of the rod in relation to the opening in the guide tube.

4. An instrument according to claim 1, wherein the guide tube comprises a pin configured to engage a recess disposed on the end wall of the intersomatic cage.

5. An instrument according to claim 1, wherein the guide tube comprises a pin configured to engage a recess disposed on the end wall of the intersomatic cage, the retaining end of the rod, the pin, and the end portion of the implantation instrument being configured to cooperate with, respectively, the end hole, the recess, and the return hole, to secure a grip on the intersomatic cage by the implantation instrument, and to facilitate the withdrawal of the instrument following implantation of the intersomatic cage by removing the retaining end of the rod from the end hole.

6. An instrument for implantation of an intersomatic cage for an intervertebral fusion graft comprising a body generally defining an arc, the body comprising a lateral concave surface; a lateral convex surface; a substantially transverse upper surface; a substantially transverse lower surface; an end wall at a first longitudinal extremity of the body, the end wall comprising an end hole oriented substantially tangential to the arc defined by the body; said instrument comprising:

a rod comprising a retaining end configured for insertion in the end hole;

a gripping end for gripping the intersomatic cage, the gripping end comprising a support spatula comprising:

a base and generally defining an arc complementary to the arc defined by the body, a guide tube in which the rod is slidably disposed and to which the base of the support spatula is mounted, the guide tube comprising an opening through which the retaining end of the rod can transit for insertion in the end hole;

a handling end for manipulating the instrument, wherein the support spatula is configured to engage the intersomatic cage along the lateral concave surface; and an aiming tube that extends substantially to the vicinity of the handling end of the instrument, wherein the guide tube comprises a mobile portion that pivots in relation to the aiming tube at least in a primary pivot direction, the primary pivot direction lying substantially within a plane in which the arc defined by the support spatula lies, and the position of the mobile portion in relation to the aiming tube defining a pivot angle.

7. An instrument according to claim 6, wherein one of the mobile portion or the aiming tube comprises a substantially spherical end, and the other of the mobile portion or the aiming tube comprises a recessed end having a shape and dimensions complementary to the shape and dimensions of the spherical end, the spherical end and the recessed end being configured, respectively, as a ball component and a socket component of a ball and socket connection.

8. An instrument according to claim 7, wherein the socket component comprises opening edge portions, one of which portions is proximal to the support spatula and is configured to encompass the ball component less than the other opening edge portions to allow further pivoting of the mobile portion in relation to the aiming tube at least in the primary pivot direction.

9. An instrument according to claim 7, wherein the rod is flexible and slidably transits the ball and socket connection through a channel located at the centre of the ball component and the socket component, the channel having a hollowed portion proximal to the support spatula, the hollowed portion configured to allow the rod to slide through the ball and socket connection even when the mobile portion is pivoted in relation to the aiming tube.

10. An instrument according to claim 6, the instrument further comprising a lock slidably disposed along the aiming tube, the lock having a forward position and being configured to fix the mobile portion of the guide tube at a selected pivot angle when the lock is disposed in the forward position.

11. An instrument according to claim 10, wherein the mobile portion comprises a serration configured to increase the maximum pivot angle at which the mobile portion of the guide tube can be fixed by the lock and to provide a predetermined pivot angle.

12. An instrument according to claim 11, wherein the serration is configured for engagement with the lock without disposing the lock in the forward position, said engagement establishing a pre-determined pivot angle and preventing pivoting of the mobile portion.

13. An instrument according to claim 1, wherein the handling end of the instrument comprises a handle configured to allow the manipulation of the instrument and to facilitate the implantation of the intersomatic cage between the vertebrae.

14. An instrument for implanting an intersomatic cage, the instrument comprising:

a rod including a retaining end configured for insertion in an end hole in an end wall at a first longitudinal extremity of a body of the intersomatic cage;

a gripping end for gripping the intersomatic cage, the gripping end comprising a support spatula configured to engage a lateral concave surface of the intersomatic cage, the support spatula comprising:

a base and generally defining an arc complementary to an arc defined by the body of the intersomatic cage, a guide tube in which the rod is slidably disposed and to which the base of the support spatula is mounted, the guide tube including an opening through which the retaining end of the rod can transit for insertion in the end hole; and a handle disposed opposite the base for manipulating the instrument, wherein the support spatula comprises an end portion distal from the base, the end portion configured for insertion into a return hole disposed on an incurvate return part of the intersomatic cage, which return hole is oriented substantially tangential to the arc defined by the body.

* * * * *